United States Patent
Miller et al.

(10) Patent No.: US 9,457,013 B2
(45) Date of Patent: *Oct. 4, 2016

(54) METHOD FOR TREATING A NEUROLOGICAL DISORDER ASSOCIATED WITH HYPOXIA USING A SMALL MOLEUCULE MIF INHIBITOR

(71) Applicant: THE FEINSTEIN INSTITUTE FOR MEDICAL RESEARCH, Manhasset, NY (US)

(72) Inventors: Edmund Miller, Huntington, NY (US); Yousef Al-Abed, Dix Hills, NY (US); Yinzhong Zhang, Oakland Gardens, NY (US); Kai Fan Cheng, Brooklyn, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 1 day.

This patent is subject to a terminal disclaimer.

(21) Appl. No.: 14/276,104

(22) Filed: May 13, 2014

(65) Prior Publication Data

US 2014/0242091 A1   Aug. 28, 2014

Related U.S. Application Data

(63) Continuation of application No. 13/528,350, filed on Jun. 20, 2012, now Pat. No. 8,741,299.

(60) Provisional application No. 61/498,936, filed on Jun. 20, 2011.

(51) Int. Cl.
| | |
|---|---|
| *A61K 39/395* | (2006.01) |
| *A61K 31/42* | (2006.01) |
| *C07K 16/24* | (2006.01) |
| *A61K 39/00* | (2006.01) |

(52) U.S. Cl.
CPC .............. *A61K 31/42* (2013.01); *C07K 16/24* (2013.01); *A61K 2039/505* (2013.01); *C07K 2317/70* (2013.01)

(58) Field of Classification Search
CPC ............................... A61K 31/42; C07K 16/24
See application file for complete search history.

(56) References Cited

U.S. PATENT DOCUMENTS 4,914,101 A    4/1990   Marfat

OTHER PUBLICATIONS

Zhang Y et al., entitled "MIF in Hypoxic Pulmonary Vascular Remodeling and Cell Proliferation," Meeting Abstracts of 9th International PH Conference and Scientific Sessions, Jun. 24-27, 2010.
Zhang Y et al., entitled "Macrophage Migration Inhibitory Factor Mediates Hypoxia-Induced Pulmonary Hypertension," Molecular Medicine 18:215-223, 2012.
Baugh and Donnelly, J. Endocr., 179:15-23, 2003.
Peitte et al., JBC 284: 32483-32492, 2009.

*Primary Examiner* — Gyan Chandra
(74) *Attorney, Agent, or Firm* — Amster, Rothstein & Ebenstein LLP

(57) ABSTRACT

Methods are provided for treating pathologies associated with hypoxia with an MIF inhibitor. Methods are also provided for treating a subject having, or at risk for pulmonary hypertension, with an MIF inhibitor. Methods are also provided for reating a subject having, or at risk from, a CNS disorder associated with hypoxia, with an MIF inhibitor. Methods are also provided of treating severe chronic lung disease, hypoxia-induced right ventricular hypertrophy or hypoxia-induced pulmonary vascular remodeling with an MIF inhibitor. Methods of diagnosing a subject with pulmonary hypertension are also provided.

12 Claims, 11 Drawing Sheets

METHOD FOR TREATING A NEUROLOGICAL DISORDER ASSOCIATED WITH HYPOXIA USING A SMALL MOLEUCULE MIF INHIBITOR

CROSS-REFERENCE TO RELATED APPLICATIONS

This application is a continuation of U.S. patent application Ser. No. 13/528,350, filed Jun. 20, 2012, now allowed, which claims the benefit of U.S. Provisional Patent Application No. 61/498,936, filed Jun. 20, 2011, the contents of each of which are herein incorporated by reference in their entirety.

SEQUENCE LISTING INCORPORATION

The ".txt" Sequence Listing filed by EFS, and which is entitled 50425-479_ST25.txt, is 12 kilobytes in size and was created on May 13, 2014, is hereby incorporated by reference.

BACKGROUND OF THE INVENTION

Throughout this application various publications are referred to by number or name in parentheses. The disclosures of these publications, as well as all patents, patent application publications and books cited herein, are hereby incorporated by reference in their entirety into the subject application to more fully describe the art to which the subject invention pertains.

Hypoxia can cause problem responses in multiple body systems, including the pulmonary system and the central nervous system.

Pulmonary hypertension (PH) is a devastating disease associated with progressive hypoxemia, right ventricular failure, and a mortality rate of around 50% within three years of diagnosis (1). Pulmonary hypertension can occur in association with chronic lung disorders, and in these cases hypoxia plays a pivotal role in the pulmonary hypertension etiology. Hypoxia induces pulmonary vessel constriction and persistent hypoxia results in pulmonary vascular remodeling involving proliferation of endothelial cells, smooth muscle cells (SMC), and fibroblasts, resulting in vessel wall thickness and vessel narrowing (2, 3). Pulmonary vascular remodeling permanently increases pulmonary circulation resistance, leading to right ventricular failure, decreased left ventricular preload and reduced cardiac output. Pulmonary vascular remodeling also causes mismatch of the blood flow and the ventilation (V/Q), which, along with decreased cardiac output and possible cardiac shunt, leads to further hypoxia. Rapid progression of pulmonary hypertension symptoms may be due in part to its cyclical nature. Thus, pulmonary hypertension can be initiated by hypoxia, itself causes hypoxia, and hypoxia in turn exacerbates pulmonary hypertension. Although the pathogenesis remains to be clarified, the current evidence suggests that hypoxia-induced pulmonary vascular remodeling is a chronic inflammatory response, and inflammatory cell proliferation plays a key role in this process (2, 4).

As is well known in the art, hypoxia also causes problem responses and pathologies in other body systems. For example, hypoxia causes regional changes in the brain including neurogenesis, hippocampal atrophy, transcriptional factor upregulation, and altered protein expression. These changes are associated with impaired sleep quality, mental performance, productivity, and general well-being, among other central nervous system complications.

Macrophage migration inhibitory factor (MIF) is a potent proinflammatory cytokine involved in both chronic and late stage acute inflammation (5), and it has been shown previously that the lungs can be a major source of this inflammatory protein (6). MIF can increase proliferation of several cell types including those relevant to the vasculature, i.e. fibroblasts (7-12), endothelial cells (13), and SMCs (14, 15). Hypoxia is known to induce MIF expression in certain systems through the hypoxia-inducible factor-1 alpha (HIF-1α) pathway (16-20). Furthermore, MIF amplifies hypoxia-induced HIF-1α stabilization in certain systems, leading to a positive feedback and induction of further MIF and expression of other HIF-1 related factors (18, 21).

Current therapies for pulmonary hypertension and other pathologies associated with hypoxia are limited. There exists a need for new therapeutics for the treatment of pulmonary hypertension and also for other consequences of hypoxia.

SUMMARY OF THE INVENTION

The present invention provides a method for treating a disorder associated with hypoxia in a subject comprising administering to the subject an amount of a macrophage migration inhibitory factor (MIF) inhibitor effective to treat the disorder associated with hypoxia.

The present invention provides a method for treating pulmonary hypertension in a subject comprising administering to the subject an amount of a macrophage migration inhibitory factor (MIF) inhibitor effective to treat pulmonary hypertension.

The present invention also provides a method for treating a subject at risk for pulmonary hypertension comprising administering to the subject an amount of a macrophage migration inhibitory factor (MIF) inhibitor effective to inhibit the development of pulmonary hypertension.

The present invention also provides a method for treating severe chronic lung disease in a subject comprising administering to the subject an amount of a macrophage migration inhibitory factor (MIF) inhibitor effective to treat severe chronic lung disease.

In addition, the present invention provides a method for treating hypoxia-induced right ventricular hypertrophy or hypoxia-induced pulmonary vascular remodeling in a subject comprising administering to the subject an amount of a macrophage migration inhibitory factor (MIF) inhibitor effective to treat hypoxia-induced right ventricular hypertrophy or hypoxia-induced pulmonary vascular remodeling.

Also provided is a method for diagnosing hypoxia-induced pulmonary hypertension in a subject comprising obtaining a sample of the subject's plasma and determining the level of macrophage migration inhibitory factor in the sample, wherein a level of macrophage migration inhibitory factor in excess of a predetermined control level indicates that the subject has hypoxia-induced pulmonary hypertension.

The present invention provides a method for treating a mental or neurological disorder associated with hypoxia in a subject comprising administering to the subject an amount of a macrophage migration inhibitory factor (MIF) inhibitor effective to treat the mental or neurological disorder associated with hypoxia.

Additional objects of the invention will be apparent from the description which follows.

DETAILED DESCRIPTION OF THE INVENTION

Figure 1:
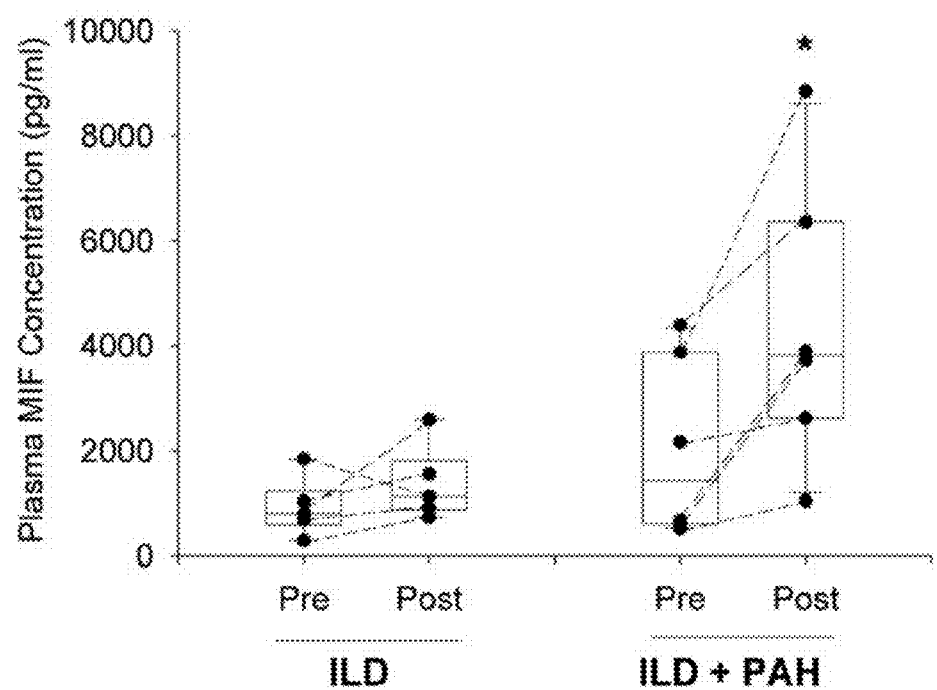
FIG. 1: Effect of exercise on venous plasma MIF concentration. Following 10 minutes exercise, adjusted to the patient's target heart rate, four of five patients in the interstitial lung disease (ILD) group had increased plasma MIF concentrations although the overall increase was not statistically significant. However, in all seven individuals of the ILD plus pulmonary hypertension group, the plasma MIF was significantly increased post-exercise (p=0.02), and the post-exercise plasma MIF concentrations were significantly different between the ILD-PH and ILD groups (p=0.04).

The present invention provides a method for treating pathologies associated with hypoxia in a subject by administering to the subject an amount of a macrophage migration inhibitory factor (MIF) inhibitor effective to treat the pathology associated with hypoxia.

The present invention provides a method for treating pulmonary hypertension in a subject by administering to the subject an amount of a macrophage migration inhibitory factor (MIF) inhibitor effective to treat pulmonary hypertension. In the method of this invention, the subject may be diagnosed with pulmonary hypertension or suspected of having pulmonary hypertension.

In accordance with the present invention, "pulmonary hypertension" is a disease state manifesting an increase in blood pressure in the pulmonary artery, pulmonary vein, and/or pulmonary capillaries leading to shortness of breath, dizziness, fainting, and other symptoms, which are exacerbated by exertion. Pulmonary hypertension can be a severe disease with a markedly decreased exercise tolerance and heart failure. In a preferred embodiment, pulmonary hypertension describes the state where the subject's mean pulmonary artery pressure exceeds 25 mm Hg (3333 Pa) at rest, or 30 mm Hg (4000 Pa) with exercise.

In accordance with the present invention, the term "pulmonary hypertension" includes but is not limited to hypoxia-induced pulmonary hypertension, sporadic primary pulmonary hypertension, familial primary pulmonary hypertension, idiopathic pulmonary arterial hypertension, primary pulmonary hypertension, or secondary pulmonary hypertension. Preferably, the pulmonary hypertension is hypoxia-induced pulmonary hypertension.

As used herein, the pulmonary hypertension can result from an autoimmune condition or be non-autoimmune. As used herein, pulmonary hypertension states with autoimmune etiologies include those by, for example, lung damage resulting from scleroderma or rheumatoid arthritis. "Non-autoimmune" with regard to a disease state of pulmonary hypertension means a disease state of pulmonary hypertension which does not have an autoimmune etiology. In the preferred embodiment, the pulmonary hypertension is not associated with an autoimmune etiology (i.e., is non-autoimmune).

As used herein, "treating" pulmonary hypertension means inhibiting, reducing, attenuating, stopping or reversing the progression of pulmonary hypertension. In the preferred embodiment, the pulmonary hypertension is treated by inhibiting, reducing, attenuating, stopping or reversing the progression of hypoxia-induced pulmonary vascular remodeling and/or hypoxia-induced right ventricular hypertrophy, and most preferably by inhibiting, reducing, attenuating, stopping or reversing the progression of hypoxia-induced pulmonary vascular remodeling. As a result of inhibiting, reducing, attenuating, stopping or reversing the progression of pulmonary hypertension, symptoms associated with pulmonary hypertension, or other parameter(s) by which the disease is characterized, such as mean pulmonary arterial pressure, may be reduced.

The present invention also provides a method for treating a subject at risk for pulmonary hypertension comprising administering to the subject an amount of a macrophage migration inhibitory factor (MIF) inhibitor effective to inhibit the development of pulmonary hypertension.

As used herein, a subject at risk for pulmonary hypertension is a subject having hypoxia-induced pulmonary vascular remodeling and/or hypoxia-induced right ventricular hypertrophy that renders the subject at risk for developing pulmonary hypertension.

In addition, since many patients with pulmonary hypertension also have severe chronic lung disease such as chronic pulmonary obstructive disease or interstitial lung disease, the present invention can also be used for the treatment of severe chronic lung disease such as chronic pulmonary obstructive disease or interstitial lung disease.

As used herein, "treating" severe chronic lung disease means inhibiting, reducing, attenuating, stopping or reversing the progression of severe chronic lung disease. In a preferred embodiment the subject has pulmonary hypertension and the treatment inhibits, reduces, attenuates, stops or reverses the progression of the pulmonary hypertension.

In addition, the present invention provides a method for treating hypoxia-induced right ventricular hypertrophy or hypoxia-induced pulmonary vascular remodeling in a subject comprising administering to the subject an amount of a macrophage migration inhibitory factor (MIF) inhibitor effective to treat hypoxia-induced right ventricular hypertrophy or hypoxia-induced pulmonary vascular remodeling.

As used herein, "treating" hypoxia-induced right ventricular hypertrophy or hypoxia-induced pulmonary vascular remodeling means inhibiting, reducing, attenuating, stopping or reversing the progression of hypoxia-induced pulmonary vascular remodeling and/or hypoxia-induced right ventricular hypertrophy.

In an embodiment the subject does not have chronic obstructive pulmonary disease or chronic pulmonary inflammatory disease.

In the methods of the present invention, the MIF inhibitor can be any agent that inhibits MIF that is capable of treating pulmonary hypertension, hypoxia-induced pulmonary vascular remodeling, hypoxia-induced right ventricular hypertrophy, or severe lung disease as defined herein.

The present invention also provides a method for treating a disorder associated with hypoxia in a subject comprising administering to the subject an amount of a macrophage migration inhibitory factor (MIF) inhibitor effective to treat the disorder associated with hypoxia.

In an embodiment, the disorder associated with hypoxia is pulmonary hypertension.

In an embodiment, the disorder associated with hypoxia is neurological or is a mental disorder. In an embodiment, the disorder is a cognitive dysfunction, anxiety, depression, or a memory deficit. In a preferred embodiment, the disorder is a memory deficit. In an embodiment, the disorder is a working memory deficit. In an embodiment, the disorder is a spatial working memory deficit.

By way of example, the MIF inhibitors of the invention can be a small molecule or an antibody or antibody fragment. Preferably, the MIF inhibitor is well-tolerated in a physiological setting. As used herein, a "small molecule" is an organic molecule which is not a polymer and which is 2000 Da or less. In an embodiment, the small molecule is 1000 Da or less.

By way of example, suitable MIF inhibitors include but are not limited to MIF inhibitors described in Yousef Al-Abed et al., U.S. Patent Application Publication No. 2009-0137647 A1 published May 28, 2009; U.S. Patent Application Publication No. US 2009-0170951 A1; U.S. Patent Application Publication No. US 2008-0305118 A1; U.S. Patent Application Publication No. US 2009-0318509 A1; U.S. patent application Ser. No. 12/735,161, filed Sep. 8, 2010, Y. Al-Abed et al.; U.S. Patent Application Publication No. 20080113997, published May 15, 2008; U.S. Patent Application Publication No. 20100016391, Y. Al-Abed, published Jan. 21, 2010; U.S. Patent Application Publication No. 20070179132, Sircar, Aug. 2, 2007; U.S. Patent Application Publication No. 20070179149, Sircar, published Aug. 2, 2007; U.S. Patent Application Publication No. 20070191388, published Aug. 16, 2007; U.S. Patent Application Publication No. 20070197547, Gaeta, published Aug. 23, 2007, the contents of each of which are hereby incorporated by reference. In an embodiment, the MIF inhibitor is a small molecule which does not comprise an oxazinone. Preferably, the MIF inhibitor is selected from the inhibitors described in Yousef Al-Abed et al., U.S. Patent Application Publication No. 2009-0137647 A1 published May 28, 2009. Preferably, the MIF inhibitor has the following structure:

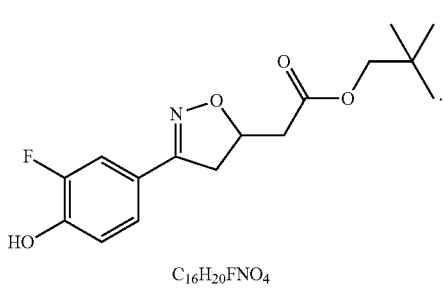

ISO-92

$C_{16}H_{20}FNO_4$

ISO-92 has a single chiral center and occurs as R and S enantiomers and may be prepared as a racemic mixture, an enantiomerically-enriched mixture or as pure isomers. In an embodiment, the MIF inhibitor is an S-isomer of ISO-92. In an embodiment, the MIF inhibitor is an R-isomer of ISO-92. In an embodiment, the MIF inhibitor is a racemate of ISO-92. In an embodiment, the MIF inhibitor is an enantiomerically enriched ISO-92.

The MIF inhibitor can be an antibody or fragment thereof directed against MIF. The MIF inhibitor can be an RNAi-based MIF inhibitor. The MIF inhibitor can be an siRNA directed against MIF or an shRNA directed against MIF. The MIF inhibitor can be one set forth in Orita et al., Macrophage migration inhibitory factor and the discovery of tautomerase inhibitors, *Curr Pharm Des.* 2002; 8(14):1297-317, the contents of which are hereby incorporated by reference.

The MIF inhibitor can be an antibody MIF inhibitor or antibody fragment MIF inhibitor directed against a MIF comprising SEQ ID NO: 1. In an embodiment, the MIF inhibitor can be an antibody MIF inhibitor or antibody fragment MIF inhibitor directed against the following sequence:

of the heavy chain and/or the constant region of the light chain, with corresponding regions from a human immunoglobulin light chain or heavy chain) (see, e.g., Cabilly et al., U.S. Pat. No. 4,816,567; Morrison et al., Proc. Natl. Acad. Sci. 81: 6851-55, 1984). Chimeric antibodies reduce the immunogenic responses elicited by animal antibodies when used in human clinical treatments. In addition, recombinant humanized antibodies may be synthesized. Humanized antibodies are antibodies initially derived from a nonhuman mammal in which recombinant DNA technology has been used to substitute some or all of the amino acids not required for antigen binding with amino acids from corresponding regions of a human immunoglobulin light or heavy chain. That is, they are chimeras comprising mostly human immunoglobulin sequences into which the regions responsible for specific antigen-binding have been inserted (see, e.g., PCT patent application WO 94/04679). Animals are immunized with the desired MIF antigen, the corresponding antibodies are isolated and the portion of the variable region sequences responsible for specific antigen binding are removed. The animal-derived MIF antigen-binding regions are then cloned into the appropriate position of the human antibody genes in which the antigen binding regions have been deleted. Humanized antibodies minimize the use of heterologous (inter-species) sequences in antibodies for use in human therapies, and are less likely to elicit unwanted immune responses. Primatized antibodies can be produced similarly.

Another embodiment of the antibodies employed in the compositions and methods of the invention is a human antibody directed against MIF, which can be produced in nonhuman animals, such as transgenic animals harboring one or more human immunoglobulin transgenes. Such animals may be used as a source for splenocytes for producing hybridomas, as is described in U.S. Pat. No. 5,569,825.

Antibody fragments and univalent antibodies may also be used in the methods and compositions of this invention. Univalent antibodies comprise a heavy chain/light chain dimer bound to the Fc (or stem) region of a second heavy chain. "Fab region" refers to those portions of the chains

```
                                                          (SEQ ID NO: 1)
  1 MPMFIVNTNV PRASVPDGFL SELTQQLAQA TGKPPQYIAV HVVPDQLMAF GGSSEPCALC

61 SLHSIGKIGG AQNRSYSKLL CGLLAERLRI SPDRVYINYY DMNAANVGWN NSTFA.
```

In an embodiment, the MIF is mammalian MIF. In an embodiment, the MIF is human MIF.

As used herein, the term "antibody" refers to complete, intact antibodies. As used herein "antibody fragment" refers to Fab, Fab', F(ab)2, and other antibody fragments, which fragments (like the complete, intact antibodies) bind the antigen of interest, in this case MIF. In an embodiment, the anti-MIF antibody fragment is an scFv.

Complete, intact antibodies include, but are not limited to, isolated monoclonal antibodies such as human or murine monoclonal antibodies, polyclonal antibodies, chimeric antibodies, human antibodies, and humanized antibodies.

Various forms of antibodies for use in the present invention as inhibitors of MIF may be produced using standard recombinant DNA techniques (Winter and Milstein, Nature 349: 293-99, 1991). For example, "chimeric" antibodies may be constructed, in which the antigen binding domain from an animal antibody is linked to a human constant domain (an antibody derived initially from a nonhuman mammal in which recombinant DNA technology has been used to replace all or part of the hinge and constant regions which are roughly equivalent, or analogous, to the sequences which comprise the Y branch portions of the heavy chain and to the light chain in its entirety, and which collectively (in aggregates) have been shown to exhibit antibody activity. A Fab protein includes aggregates of one heavy and one light chain (commonly known as Fab'), as well as tetramers which correspond to the two branch segments of the antibody Y, (commonly known as $F(ab)_2$), whether any of the above are covalently or non-covalently aggregated, so long as the aggregation is capable of specifically reacting with a particular antigen or antigen family.

The antibody can be, e.g., any of an IgA, IgD, IgE, IgG, or IgM anti-MIF antibody. The IgA antibody can be, e.g., an IgA1 or an IgA2 antibody. In an embodiment the antibody is an immunoglobulin G. In an embodiment the antibody fragment is a fragment of an immunoglobulin G. In an embodiment the antibody is, or the fragment is of, an IgG1, IgG2, IgG2a, IgG2b, IgG3 or IgG4. A combination of any of these antibodies subtypes can also be used. One consideration in selecting the type of antibody to be used is the desired serum half-life of the antibody. IgG has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000). Another consideration is the size of the antibody. For example, the size of IgG is smaller than that of IgM allowing for greater penetration of IgG into tissues.

As used herein, the term "bind", or grammatical equivalent, means the physical or chemical interaction between two proteins or compounds or associated proteins or compounds or combinations thereof, including the interaction between an antibody and a protein. Binding includes ionic, non-ionic, hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates.

Another agent useful for these methods that inhibits activity of the MIF is an aptamer that binds specifically to the MIF. Aptamers are single stranded oligonucleotides or oligonucleotide analogs that bind to a particular target molecule, such as MIF. Thus, aptamers are the oligonucleotide analogy to antibodies. However, aptamers are smaller than antibodies, generally in the range of 50-100 nt. Their binding is highly dependent on the secondary structure formed by the aptamer oligonucleotide. Both RNA and single stranded DNA (or analog), aptamers are known. See, e.g., U.S. Pat. Nos. 5,773,598; 5,496,938; 5,580,737; 5,654,151; 5,726,017; 5,786,462; 5,503,978; 6,028,186; 6,110,900; 6,124,449; 6,127,119; 6,140,490; 6,147,204; 6,168,778; and 6,171,795. Aptamers can also be expressed from a transfected vector (Joshi et al., 2002, J. Virol. 76,6545).

Aptamers that bind to virtually any particular target can be selected by using an iterative process called SELEX, which stands for Systematic Evolution of Ligands by Exponential enrichment (Burke et al., 1996., J. Mol. Biol. 264, 650; Ellington and Szostak, 1990, Nature 346,818; Schneider et al., 1995, Biochemistry 34, 9599; Tuerk and Gold, 1992, Proc. Natl. Acad. Sci. USA 89:6988; Tuerk and Gold, 1990, Science 249:505). Several variations of SELEX have been developed which improve the process and allow its use under particular circumstances. See, e.g., U.S. Pat. Nos. 5,472,841; 5,503,978; 5,567,588; 5,582,981; 5,637,459; 5,683,867; 5,705,337; 5,712,375; and 6,083,696. Thus, the production of aptamers to any particular peptide, including MIF, requires no undue experimentation.

In an embodiment, the inhibitor of MIF is an inhibitor of human MIF.

The MIF inhibitor can be an shRNA or siRNA inhibitor of MIF directed against an mRNA encoded by NCBI Reference Sequence: NG_012099.1, or by the following human MIF sequence:

```
                                                           (SEQ ID NO: 2)
   1 cacccaccca gccggaattg gctctggcca ctctgggagg gcggggtggg ggttgcaagt 61 cccttgttac gcagggagcc cctcagttag ggagaggaga cagggtctca ggacaggacc 121 ttgaagacaa ggaagggcag tgcagagagg ggtgagagag ccagactggg tttctagggg 181 gtggtccagg gtgggagctg acctgcctct gctgagactg cgttccaggt gtgagcattg 241 atgtctagcc catgtagctg gagaggagtc acagccatgc tccccagctc cagcccacct 301 ccccagaccc cagacccagt gtggcctctc cccacctccc agagcatgtg gtcaagcccc 361 tctcctagcc cgaatccctc cctcatttgc taattaccag gacctacatg tcccagcttc 421 ccagggccag gggacagggc cccgcccatc tggcaggctc aagttggctg cctggctgcc 481 gggatccagg cggcgctcac aaggatctgg gcttgcacag cctccaaagg gctgttgtcc 541 attctcttgt atttgttctc atcctctcct ttcttggacc ctctgagtct ctggttccct 601 cttgttggga cccagatcac tctgtgcctc agctgaatca tttttcccctt cagtttacac 661 atatccacct agggtccact acatccagag gcttccgcct cagtccttgt cctcaggctg 721 tgcccagggt tgtgaggatg gcggtggtcc ttaccttgca aaacagtctc ccagtgacaa 781 caatgttcag ggataacatc tatggagggc tttctatgta tcaggaccat tctgagtatc 841 ttccaagtgt tagctccttt aatcctggaa aggaccccat gaaattagta cttttattac 901 ccctgttgta catatgagag actgagtaaa agccggtggc ttgtccaggg tcacacagct 961 aactggaatg gccaggagta gacctggtga ccatggaccc cagaccttga tcactgcaca 1021 cgctgcgtct gggacctcgc ctggtacctg aggtccgtgg cgcgctggtg ctgatcattc 1081 agagtgctca tgggaagtgt agtctagagt ctgtgtgctt cctgatctcc ttgatctcca 1141 ttttattgag gaggccttta ggccacccga ggggtccaga gtgaccctgt ggattagcag 1201 tggagctcag cttgagccag cgctcttcag gggtcgtgtt ctgcccccat tctctggttc 1261 attctgcagg tagcagggaa tcattgaaga ttagagagaa tcaaacacct ggagagagat 1321 gactctgccc ggggagccca ggctcctgtc tgggtgcaca ctccagggct agatggtgac
```

-continued

```
1381 ttctcagcta ctctagcttc ataggctcat agagcatgtg agcactcatg tggacacacg 1441 tgcacgcgca cacacatgga cacacacaca cacacacaca ccgctgtctt tggaatcaga 1501 ccatgaaaat gcttcctcag aggcctaggg gtgaggaagc tgaggtgagt tgtgcctcca 1561 gctggatgtg ctgggatggg gtgggagatg aggtggccac acctgggtgg caggaactct 1621 ggggcagtga accttctaac gaacagatct gggatgctgc catgaggagg aagagggagt 1681 cagcagccat gcctgccaat gcctcctagc gcatttgtcc atggttagcg ataattatt 1741 gtgtccctat gggtcccaag gtgtattatt ttttttttgc tcttataata aatcaacaca 1801 aattttagc agcttcaaac aacacgcatt tattatctca cagtttctgt gggtcaggag 1861 tccggcgtga catgactagg tcttctgtgt aaggactcgc atggccaaag tcaaggtatc 1921 tgaaggaca agggaaaaat ccacttccaa gttcaatctg gttgtgagca gaattcagtt 1981 ccttgtggtt gtaccatgag gtctctggtc cccttcatct tcaaagccgg taatggacat 2041 cgagtgtttc tcttgcttgg aatctggcac tctagctgga gaaaattatc tgcttttaag 2101 agttcatgtg attagattgg gtgtacccag atgctccatg ctaatctccc tattatgcac 2161 agatgcataa tcctaattgc atctgtgaag tgcttttttgc caggtaacat ggcatacttg 2221 taggttccag ggattagtgc ttgtcctccc cctgctattc tttagtgggc aggggtcat 2281 ctgcctacca cggaggtaag gggtcaggag gtatgcatac agcaatgccc aaaaagagac 2341 tgtccccact gggatggagt ttaccgccta gacatgcagt cttaactcag aaatatggag 2401 atagcctcga aggacaggac aggtactggg cacgtgtggg aatggaccaa gccaggtgct 2461 ccgggggctt tcccaaggaa ctaaggctga gccaagaact gaaggatgag ttggagtcag 2521 atgagggaaa atgtgggcaa actggatttc agaaccaacc cccaaccctg gagccaggag 2581 ccatggtact gaaggacagt gcgccataac tcagagaacc agggagggtt ggcggaggct 2641 cacagggacc gggttaccccc agggccttgt gacagtacta cccctagtat cagaggagac 2701 tgtcattggc atttaggcca cttggtgctc ataacacctc tatgtcaggt gaacactatt 2761 gtcatcccca aattacagat ggggaaagtg agccaaatgt ccatgctagt aagaggcaaa 2821 tcatatcact tctttgggta cccttctaga aggatgaggc tgactgccac tggaaacagc 2881 tggggagggt acaaggagat gacaagtggc tcagaggctg tcctggctat aagaattaaa 2941 gaggaaagaa acaccaaggg tggctcgaca gtcaacaagg acaggtttat tttggaaaac 3001 aaacttgaga ggggcttctg gccaagttag gtcagagcca cactctctta caaactaagg 3061 atatttaagg gttttggagg gggttcttat cataggttct gaatgtttct gtgtgaggga 3121 aagtttattg cggggatgga atgtctctgg tcagaaggga ggctgtctcc gggttggcat 3181 gtttctggtc agagaagggt ttatcttagg gttggaatgt ttctggttat gctgacatta 3241 gctattaggc tgatattttc gggctggatt taggcggctt ttaattaagg gggaacttag 3301 aatggtggtg tttgttcaag atggcaatgc tcctgctccg tcactggcca ggtaaggcaa 3361 cccttttgtta tggtaacaac ctgagattgg caggggctca cctccagggg cagctcatgt 3421 gcttgctggc gaggctgcac cttgtcattc aggttcacag gcacaggtc aaccaggccc 3481 tggctcttca gtcttctgcc tggagtgact tatgtaattc tgctcagctt tcatagggca 3541 cagggagtcg gggctaactc tgctgcctgg ggctggaaac agactcctcc cttgaggagc 3601 agcagtccac catagggaag tcacagtggt ccaggccaaa ggggatgcag gtagtgtaga 3661 ctaggcggta gttcagggaa tggagagaag tgggaataaa gggatagtga aaggaagcat 3721 attttactgg caggtgatga ggtgtaggag gacaagtcat acatttggac tttacagagc 3781 agtggacact cagtcagctg ctgtcagcgc ctgggactta ggggagtgcc cctggctgga
```

-continued

```
3841 gacatggtat ggagtgccat cagttaggga gccctgggca caggtaagag aaggtgtgac
3901 accaggaggg aaagagtctg gggcccagct gcaggaacca atacccatag gctatttgta
3961 taaatgggcc atggggcctc ccagctggag gctggctggt gccacgaggg tcccacaggc
4021 atgggtgtcc ttcctatatc acatggcctt cactgagact ggtatatgga ttgcacctat
4081 cagagaccaa ggacaggacc tccctggaaa tctctgagga cctggcctgt gatccagttg
4141 ctgccttgtc ctcttcctgc tatgtcatgg cttatcttct ttcacccatt cattcattca
4201 ttcattcagc agtattagtc aatgtctctt gtatgcctgg cacctgctag atggtccccg
4261 agtttaccat tagtggaaaa gacatttaag aaattcacca agggctctat gagaggccat
4321 acacggtgga cctgactagg gtgtggcttc cctgaggagc tgaagttgcc cagaggccca
4381 gagaagggga gctgagcacg tttgaaccac tgaacctgct ctggacctcg cctccttccc
4441 ttcggtgcct cccagcatcc tatcctcttt aaagagcagg ggttcaggga agttccctgg
4501 atggtgattc gcaggggcag ctcccctctc acctgccgcg atgactaccc cgccccatct
4561 caaacacaca agctcacgca tgcgggactg gagcccttga ggacatgtgg cccaaagaca
4621 ggaggtacag gggctcagtg cgtgcagtgg aatgaactgg gcttcatctc tggaagggta
4681 aggggccatc ttccgggttc accgccgcat ccccaccccc ggcacagcgc tcctggcga
4741 ctaacatcgg tgacttagtg aaaggactaa gaaagacccg aggcgaggcc ggaacaggcc
4801 gatttctagc cgccaagtgg agaacaggtt ggagcggtgc gccgggctta gcggcggttg
4861 ctggaggaac gggcggagtc gcccagggtc ctgccctgcg gggtcgagc cgaggcaggc
4921 ggtgacttcc ccactcgggg cggagccgca gcctcgcggg ggcggggcct ggcgccggcg
4981 gtggcgtcac aaaaggcggg accacagtgg tgtccgagaa gtcaggcacg tagctcagcg
5041 gcggccgcgg cgcgtgcgtc tgtgcctctg cgcgggtctc ctggtccttc tgccatcatg
5101 ccgatgttca tcgtaaacac caacgtgccc cgcgcctccg tgccggacgg gttcctctcc
5161 gagctcaccc agcagctggc gcaggccacc ggcaagcccc ccaggtttg ccgggagggg
5221 acaggaagag gggggtgccc accggacgag gggttccgcg ctgggagctg ggaggcgac
5281 tcctgaacgg agctggggg cggggcgggg ggaggacggt ggctcgggcc cgaagtggac
5341 gttcggggcc cgacgaggtc gctggggcgg gctgaccgcg ccctttcctc gcagtacatc
5401 gcggtgcacg tggtcccgga ccagctcatg gccttcggcg gctccagcga gccgtgcgcg
5461 ctctgcagcc tgcacagcat cggcaagatc ggcggcgcgc agaaccgctc ctacagcaag
5521 ctgctgtgcg gcctgctggc cgagcgcctg cgcatcagcc cggacaggta cgcggagtcg
5581 cggaggggcg ggggaggggc ggcggcgcgc ggccaggccc gggactgagc cacccgctga
5641 gtccggcctc ctccccccgc agggtctaca tcaactatta cgacatgaac gcggccaatg
5701 tgggctggaa caactccacc ttcgcctaag agccgcaggg acccacgctg tctgcgctgg
5761 ctccacccgg gaacccgccg cacgctgtgt ctaggcccg cccacccaa ccttctggtg
5821 gggagaaata aacggtttag agactaggag tgcctcgggg ttccttggct gcgggagga
5881 attggtgcag agccgggata ttggggagcg aggtcgggaa cggtgttggg ggcggggtc
5941 agggccgggt tgctctcctc cgaacctgct gttcgggagc ccttttgtcc agcctgtccc
6001 tcctacgctc ctaacagagg agccgcaggg tctttccatt ctatggcgta cgaagggatg
6061 aggagaagtt ggcactctgc cctgggctgc agactcggga tctaaggcgc tctgcccgcc
6121 ggaatccgtt gtacctaggg ccaccacgtg gggtgctgga ggtgagccga ccacggaaga
6181 gggggaggag gagttggagt tgggaggagt ccgaggtctt ctaggcctag acctttctct
```

```
-continued
6241 cagccccacc ttccccagcc ttcttgttgg gcagagggta gccagaggac agaaagatcc 6301 cacccagagc cactcactgc catccacttt gttaggtgac ttcaggagag ttttcaggcg 6361 ggtgggtggg ggaggtgcag agttcttggt cataccgccc cgtccacccc cgaacccac 6421 gccttgggtt ctgctcccct cagacaccca ccaagcctcc gccacagcag ttccctgagg 6481 aaattgggcg tggggtttcc attgggaccg ttcgtgttct gtggtgccac agacatgtct 6541 gtaaaacctt cagttatgtt tgggcgcagt ggcacaagcc tgtgatcccg gcactttggg 6601 aggtggaggt gagtggagtg tgactcctct gcttctctca gtctccagcc acatctcgtc 6661 tccagtcccc tgttcactcg gtcatcccgc gcagtactgg acagcgagct ctccttccag 6721 aagagcaatg gggctgggtg gggtgaagat taggaagagg aaggagaata gaagctccag 6781 ggagtctgga agggtggcac ccatcttggg atggggcacc ccttccatga aggtctctaa 6841 agcaaggccc tcctcagctt actccctgcc agccgagggc ctcagtctca ttgttaactc 6901 agtgagaggg cggtggagcc cctcgtctac ctcccagctg ggggagacat gggggggcatg 6961 ggatggctcc agctgtagcg ggaaggtccc actcctctca gcctggcttt caggcttgag 7021 gtttccttct tggatctgag tacctgtggt gtaacaggca ccctcctcgg ccctggcctt 7081 tatcacatcc cctcagctcc tgggtgcccc cagcccagc ctcccaaggc ctgaggctga 7141 gctttgccca ggaccccag ttcccccccac aacaaactct ttctgcctcg ggccccacac 7201 cccaccaagc cctggctggc cccctggctc ccaccccgcc tcagcggtct ttgctctcgg 7261 ctgtgtcaca gatagggaga gcaggggcgc agtgccccat gagcatctaa tgcaactccc 7321 tcatttcaca gatgaggaca ctgacccag gatccagggc atggtcatac actcaatgcc 7381 atgcccctg caagggccct gtggcctcac atgagcaagt tagactctga gggccgagga 7441 gatgggcagg gcaggctggg cacctgctgt gtgagggcag gagggttggt gagagctgtc 7501 ctccaaaagc aggtgagtgt ctgaggttct gtggccccct gggggcatcc acaaggtcat 7561 gggtccttgg actccaggaa caaaggggggt gtctgtgggt cagggaccta tccgcttgcc 7621 ctgcccaaag tgttcctaag tcccctggga ctaataaccg gcctgcctgc tggggaggtc 7681 agctgctaca tcccaccttc aagccacacc tgcccccatt gaccccatc ccatggccag 7741 ctccatttcc tccaaagcac aggctccact gcccaccagg tggtgggtct cttcctcaaa 7801 cccctgtttg actgcccag gacctgcagg gtcagccttg gaaat
```

The MIF inhibitor can be an appropriately targeted ribozyme or DNAzyme.

The MIF inhibitors referred to herein can be administered by any means known in the art. The MIF inhibitor, or composition comprising the MIF inhibitor, can be administered parentally, enterally or topically. The MIF inhibitor can be administered subcutaneously. The MIF inhibitor, or composition comprising the MIF inhibitor, can be administered intravenously. The MIF inhibitor, or composition comprising the MIF inhibitor, can be administered orally. The MIF inhibitor, or composition comprising the MIF inhibitor, can be administered topically. The MIF inhibitor, or composition comprising the MIF inhibitor, can be administered via an osmotic pump. The MIF inhibitor, or composition comprising the MIF inhibitor, can be administered inhalationally. The MIF inhibitor, or composition comprising the MIF inhibitor, can be administered directly into the site of the disease, e.g. injection into a pulmonary blood vessel.

The MIF inhibitor can be administered to the subject in a pharmaceutical composition comprising a carrier, such as a pharmaceutically acceptable carrier. Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution. The pharmaceutically acceptable carrier used can depend on the route of administration. The pharmaceutical composition can be formulated for administration by any method known in the art, including but not limited to, oral administration, parenteral administration, subcutaneous administration, intravenous administration, transdermal administration, intranasal administration, and administration through an osmotic mini-pump. The MIF inhibitors can be applied to the skin, for example, in compositions formulated as skin creams, or as sustained release formulations or patches.

The MIF inhibitors, or compositions comprising the MIF inhibitors, may be administered in various forms, including those detailed herein. The treatment with the MIF inhibitor may be a component of a combination therapy or an adjunct therapy, i.e. the subject or patient in need of the MIF inhibitor is treated or given another drug for the disease in conjunction with one or more of the instant MIF inhibitors.

This combination therapy can be sequential therapy where the patient is treated first with one agent and then the other, or the two are given simultaneously. These can be administered independently by the same route or by two or more different routes of administration depending on the dosage forms employed.

As used herein, a "pharmaceutically acceptable carrier" is a pharmaceutically acceptable solvent, or suspending vehicle or medium, for delivering the instant agents to the animal or human subject. The carrier may be liquid or solid and is selected with the planned manner of administration in mind. Liposomes and inert nanoparticles are also a pharmaceutically acceptable carriers.

The dosage of the MIF inhibitor administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the MIF inhibitor may comprise a single compound or mixtures thereof with other therapeutic compounds. The agents can be administered in oral dosage forms as tablets, capsules, pills, powders, granules, elixirs, tinctures, suspensions, syrups, and emulsions. The agents may also be administered in intravenous (bolus or infusion), intraperitoneal, subcutaneous, or intramuscular form, or introduced directly, e.g. by injection or other methods, into the heart and/or lung, all using dosage forms well known to those of ordinary skill in the pharmaceutical arts.

The MIF inhibitor can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The MIF inhibitor can be administered alone or mixed with a pharmaceutically acceptable carrier. This carrier can be a solid or liquid, and the type of carrier is generally chosen based on the type of administration being used. In one embodiment the carrier can be a monoclonal antibody. The active MIF inhibitor can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Examples of pharmaceutical acceptable carriers and excipients that may be used to formulate oral dosage forms of the compound used in the present invention are described in U.S. Pat. No. 3,903,297 to Robert, issued Sep. 2, 1975. Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol. 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.). All of the aforementioned publications are incorporated by reference herein.

Tablets comprising the MIF inhibitor used may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The MIF inhibitor can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines. The MIF inhibitors may be administered as components of tissue-targeted emulsions. The MIF inhibitor can also be administered in the form of nanoparticle-mediated delivery directly to the air passages of the subject.

The MIF inhibitor may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

The MIF inhibitors can be administered orally in solid dosage forms, such as capsules, tablets, and powders, or in liquid dosage forms, such as elixirs, syrups, and suspensions. They can also be administered parentally, in sterile liquid dosage forms.

In an non-limiting example, when treating a pulmonary hypoxia pathology such as pulmonary hypertension, the MIF inhibitor may be administered inhalationally, for example as an aerosol. Alternatively, the MIF inhibitor may be administered in any other one of the forms described herein.

Gelatin capsules may contain the MIF inhibitor and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The MIF inhibitors of the instant invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

In an embodiment, the MIF inhibitor is administered by inhalation, i.e. inhalationally. In an embodiment, the MIF inhibitor is delivered in a form, such as an aerosol form, to the airways of the subject. This can be useful for delivering the MIF inhibitor to the lungs of the subject, for treatment of pulmonary hypertension, for example, or for protection against hypoxia-associated cognitive dysfunction.

In an embodiment, the MIF inhibitor is administered so as to cross the blood brain barrier of the subject. In an embodiment, the MIF inhibitor is delivered in a suitable form, such as an aerosol form, to the upper nasal epithelia of the subject. In an embodiment, the MIF inhibitor is delivered in a suitable form, such as an aerosol form, to the nasal olfactory epithelia of the subject. Such a method of delivery is useful for delivering the MIF inhibitor to the central nervous system.

Parenteral and intravenous forms may also include minerals and other materials to make them compatible with the type of injection or delivery system chosen.

The MIF inhibitor compounds of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. For example, ISO-92 has a chiral center and may be used as a racemate, an enantionerically-enriched form or a pure enantiomer. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

When the structure of the MIF inhibitor compounds of this invention includes an asymmetric carbon atom such compound can occur as racemates, racemic mixtures, and isolated single enantiomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the MIF inhibitor compounds disclosed herein. Isotopes include those atoms having the same atomic number but different mass numbers. By way of general example and without limitation, isotopes of hydrogen include tritium and deuterium. Isotopes of carbon include carbon-13 and carbon-14.

It will be noted that any notation of a carbon in structures throughout this application, when used without further notation, are intended to represent all isotopes of carbon, such as $^{12}C$, $^{13}C$, or $^{14}C$. Furthermore, any MIF inhibitor compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein.

Isotopically-labeled compounds can generally be prepared by conventional techniques known to those skilled in the art or by processes analogous to those described in the Examples disclosed herein using an appropriate isotopically-labeled reagents in place of the non-labeled reagents employed.

The MIF inhibitor of the instant invention may be in a salt form. As used herein, a salt is salt of the instant MIF inhibitor compounds which has been modified by making acid or base, salts of the compounds. In the case of compounds used for treatment of pulmonary hypertension, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term pharmaceutically acceptable salt in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

Also provided is a method for diagnosing pulmonary hypertension in a subject comprising obtaining a sample of the subject's plasma and determining the level of macrophage migration inhibitory factor in the sample, wherein a level of macrophage migration inhibitory factor in excess of a predetermined control level indicates that the subject has pulmonary hypertension. In an embodiment, determining the level of macrophage migration inhibitory factor in the sample is performed by an immunochemical technique. In an embodiment, determining the level of macrophage migration inhibitory factor in the sample is performed employing a detectably-labeled anti-MIF antibody or antigen-binding fragment thereof.

Also provided is a method for diagnosing a subject as at risk for pulmonary hypertension comprising obtaining a sample of the subject's plasma and determining the level of macrophage migration inhibitory factor in the sample, wherein a level of macrophage migration inhibitory factor in excess of a predetermined control level indicates that the subject is considered as at risk for pulmonary hypertension. In an embodiment, determining the level of macrophage migration inhibitory factor in the sample is performed by an immunochemical technique. In an embodiment, determining the level of macrophage migration inhibitory factor in the sample is performed employing a detectably-labeled anti-MIF antibody or antigen-binding fragment thereof.

Also provided is a method for diagnosing hypoxia-associated cognitive dysfunction in a subject comprising obtaining a sample of the subject's plasma and determining the level of macrophage migration inhibitory factor in the sample, wherein a level of macrophage migration inhibitory factor in excess of a predetermined control level indicates that the subject has hypoxia-associated cognitive dysfunction. In an embodiment, determining the level of macrophage migration inhibitory factor in the sample is performed by an immunochemical technique. In an embodiment, determining the level of macrophage migration inhibitory factor in the sample is performed employing a detectably-labeled anti-MIF antibody or antigen-binding fragment thereof.

Also provided is a method for diagnosing a subject as at risk for hypoxia-associated cognitive dysfunction comprising obtaining a sample of the subject's plasma and determining the level of macrophage migration inhibitory factor in the sample, wherein a level of macrophage migration inhibitory factor in excess of a predetermined control level indicates that the subject is considered as at risk for hypoxia-associated cognitive dysfunction. In an embodiment, determining the level of macrophage migration inhibitory factor in the sample is performed by an immunochemical technique. In an embodiment, determining the level of macrophage migration inhibitory factor in the sample is performed employing a detectably-labeled anti-MIF antibody or antigen-binding fragment thereof.

In an embodiment of the methods described herein, the subject is afflicted with hypoxia resulting from being at high altitude, from closed circuit underwater breathing, from mask-on hypoxia training, from severe head trauma, or from chronic lung disease.

As used herein, a "predetermined control level" of macrophage migration inhibitory factor is a level of macrophage migration inhibitory factor determined as a control, e.g. from a control subject or control study, or a normalized predetermined level. In an embodiment, the predetermined level corresponds to a level generally found in patients without pulmonary hypertension.

In accordance with the methods of the present invention, the subject is a mammal Preferably, the subject is a human.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Details

Pulmonary Hypertension

Plasma MIF concentrations in human samples from patients with pulmonary hypertension both at baseline and after exercise were obtained. An in vitro hypoxia-induced cell proliferation and an in vivo mouse model were used to determine the role of MIF in hypoxia-induced pulmonary vascular remodeling and hypertension.

Methods and Materials

Human Study: All human studies received prior approval by the Institutional Review Board that oversees the conduct of research involving human subjects at the North Shore-Long Island Jewish Health System.

Seventeen patients between the ages of 18-65 yrs. with interstitial lung disease (ILD), pulmonary hypertension (PH) or PH with ILD were examined in this study. The study included 9 patients (3 males, 6 females, age range 37 to 57 years) with PH meeting a right heart catheterization (RHC) diagnosis of mean pulmonary artery pressure >25 mmHg at rest or >30 mmHg with exercise and pulmonary capillary wedge pressure <18 mmHg; 5 patients (3 males, 2 females, age range 35 to 72 years) with ILD, meeting accepted diagnostic criteria of total lung capacity (TLC)<60% and CT chest evidence of ILD; and 6 patients (2 males, 4 females, age range 54 to 76 years) with PH and ILD, meeting diagnostic criteria of PH and ILD as above. Individuals were excluded from the study if they had restrictive ventilation pattern other than ILD or significant obstructive lung disease. The plasma results in this initial study were compared to plasma MIF concentrations from a previously publish study using 53 controls that were randomly recruited from a population-based group (25).

Exercise Oximetry: Patients were instructed to walk on a treadmill for 10 minutes at a speed adjusted to the patient's target heart rate. Oxygen saturation and 3-Lead EKG and were measured continuously. If the oxygen saturation decreased to ≤90%, supplemental oxygen was given and increased by 1 liter increments. Borg Scale, vital signs taken pre- and post-exercise and venous blood samples were drawn from an antecubital vein pre- and post-exercise oximetry, and analyzed for MIF levels.

Blood Sampling and MIF Assay: Pre- and post-exercise venous blood samples were centrifuged, plasma separated and stored at −80° C. for MIF analysis. The plasma MIF level was measured using the Quantikine MIF Immunoassay (R&D Systems, Minneapolis, Minn.).

Cell culture studies: Human lung fibroblasts (CCL-210) were purchased from American Type Culture Collection (ATCC, Manassas, Va.). Cells were cultured in Eagle Minimum Essential Medium (EMEM) (ATCC, Manassas, Va.) with 10% fetal bovine serum (FBS) at 37° C., 5% $CO_2$. The cells were subcultured using standard procedures and were used for experiment during passages 3 to 10.

Primary lung fibroblasts from MIF knockout (mif −/−) or their counterpart wild type C57BL6 mice (mif +/+) were established by using outgrowth from lung explants (36). Briefly, mouse lungs were removed using aseptic technique, carefully dissected free of connective tissue and fat, and cut into small pieces (<1 mm) These lung tissue pieces were cultured in a dish containing EMEM, 10% FBS, and 1% penicillin/streptomycin, at 37° C., 5% $CO_2$ in air. Medium was changed twice a week. After about two weeks, fibroblasts had reached approximately 80% confluence. The fibroblasts were removed by trypsin and filtered using a sterilized 100-μm nylon cell strainer (Falcon) to remove any remaining tissue pieces. These primary lung fibroblasts were used for experiments during passages 2 to 6.

Cell proliferation assessments: 5-bromo-2-deoxyuridine (BrdU) incorporation measured by a commercially available kit (Calbiochem, EMD Chemical Inc., Gibbstown, N.J.) was used to quantify the fibroblast proliferation, BrdU is incorporated into the newly synthesized DNA of replicating cells (during the S phase of the cell cycle). The assay was performed according to the manufacturer's instructions. Briefly, fibroblasts were loaded into a 96-well plate with 6,000 cells ($6 \times 10^4$/ml×100 μl) per well. After attaching, cells were cultured for 72 hours in EMEM, without FBS, to achieve synchronized growth. The medium was then changed EMEM containing 1% FBS and BrdU. The cells were cultured for further 24 hours under controlled conditions (normoxia, hypoxia, MIF inhibitor). The medium was then removed and the cells were fixed. BrdU incorporated in newly synthesized DNA was detected with a BrdU antibody using chemiluminescence for quantification. In some experiments, manual, hemocytometer cell counts were also performed, to confirm the results obtained with the BrdU assay.

Hypoxia in vitro: A modular incubator chamber (Billups-Rothenberg Inc., Del Mar, Calif.) was used for the cell hypoxia studies. To induce hypoxia, the chamber was tightly closed and flushed with a gas mixture consisting of 95% nitrogen and 5% $CO_2$ until the desired ambient oxygen concentration of 1% was reached as measured using an oxygen sensor (BioSpherix, Lacona, N.Y.).

The whole chamber was put into a standard cell incubator for incubation. This method can produce a microenvironment within the chamber with 37° C., up to 1% $O_2$, 5% $CO_2$, and 100% humidity.

To examine the effects of hypoxia on MIF expression, human fibroblasts (CCL201) were seeded into two 6-well plates (BD, Franklin Lakes, N.J.) at $1 \times 10^5$/ml, 2 ml per well. After cell attachment and cell-cycle synchronization as described above, plates were incubated in normoxia or 1% hypoxia. After 24 hours, the medium from each well was collected, centrifuged, and the supernatants stored at −80° C. for MIF protein measurement using a commercial ELISA kit (R&D, Minneapolis, Minn.). Cell layers were lyzed and total RNA extracted using an RNA extraction kit (QIAGEN, Valencia, Calif.). The RNA was converted to cDNA and MIF gene expression was detected through real time qPCR method (Primer: MIF-F: accgctcctacagcaagc (SEQ ID NO:3); MIF-R: cgcgttcatgtcgtaatagttg (SEQ ID NO:4)) using the 7900 HT Fast Real-Time PCR System (AB Applied Biosystem, Foster City, Calif.).

To determine the role of MIF in the hypoxic cell proliferation, cells were incubated with ISO-92 or DMSO (vehicle controls). ISO-92 has the following structure:

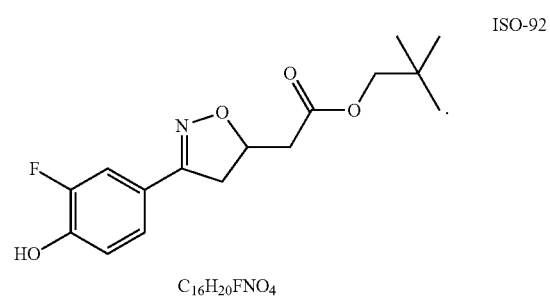 [SMILES: CC(C)(C)COC(=O)CC1CC(c2ccc(O)c(F)c2)=NO1 ; "C16H20FNO4"]

$C_{16}H_{20}FNO_4$

ISO-92 is a specific inhibitor of MIF, and was developed by rational design to fit into the hydrophobic active site of MIF (35), and synthesized in the laboratory. The hydrophobic site of MIF is required for the inflammatory activity of the molecule (37) and is associated with a tautomerase activity, which ISO-92 inhibits with an $IC_{50}$ of 0.75 μM. Cell proliferation, under both normoxic and hypoxic conditions, was then determined using the methods described above.

To further examine the role of MIF in hypoxia-induced fibroblast proliferation, the ability of primary lung fibroblasts (mif$^{-/-}$ and mif$^{+/+}$) cultured under normoxic and hypoxic conditions for 24 hrs, was assessed. To clarify the role of MIF in the proliferation, fibroblasts (mif$^{-/-}$) were cultured under hypoxic conditions, in conditioned medium (CM) in which fibroblasts (mif$^{+/+}$) had been cultured in hypoxia for 24 hr. In some cases, ISO-92 was added to this culture medium to inhibit MIF inflammatory activity.

Hypoxia in vivo: C57BL6 mice (male, 8~10 weeks old) were purchased from Taconic Farms Inc. (Hudson, N.Y.). All the animals were housed in a pathogen-free environment, under standard light and dark cycles, with free access to food and water until they were used for the experiments. All experiments involving animals were reviewed and approved by Institutional Animal Care and Use Committee of The Feinstein Institute for Medical Research.

An animal hypoxia chamber system (BioSpherix, Lacona, N.Y.) was used for the in vivo studies. With this system, a constant 10% normobaric hypoxia was achieved for up to 42 days in our study. Mice were randomly divided into 4 groups and treated with normoxia, or hypoxia for 3, 10, or 42 days. At the time of euthanasia, animals were anesthetized with isoflurane and 100% oxygen. A 26 gauge needle connected to a transducer was introduced into the right ventricular trans-diaphragmatically. The right ventricular (RV) pressure was measured and recorded using a computerized hemodynamic recording system (HAEMODYN, Harvard Apparatus, Mass.). After the RV pressure measurement, blood was taken from the RV and plasma was stored in $-80°$ C. for MIF measurement. The mice were then euthanized by exsanguination. The hearts were removed, dissected and weighed. The heart weights were expressed as a ratio of the weight of the right ventricle to the weight of the left ventricle+septum (RV/S+LV). The lung was also collected; the left side was used for measure MIF mRNA expression, and the right side fixed, at inflation, in 4% paraformaldehyde for lung vascular histology study.

To investigate the effects of MIF inhibition on hypoxia induced pulmonary vascular remodeling and hypertension, mice were randomized into 4 groups (n=5/group), and were administered DMSO (vehicle control) or ISO-92 (1.8 mg/kg/day, s.c.) via an osmotic delivery device (Alzet, Calif.) Immediately after sub-cutaneous pump implantation on the dorsum of the animals, the mice were put into hypoxia chamber undergoing 10% normobaric hypoxia for 10 days or 21 days. At the indicated times, the RV pressure, heart weight (RV/S+LV), and vascular changes were determined in each group using the methods described above.

Vascular wall thickness: Lung tissues were immunostained using anti α-smooth muscle actin (α-SMA) antibody (Abcam Inc, Cambridge Mass.) to reveal the muscular layer of the vessel wall. External diameter (ED) and internal diameter (ID) of 50 alveolar vessels (with ED of 40 to 100 µm) per animal were determined and recorded, by an independent investigator blinded to the sample's origin. The total wall thickness (WT) was measured as the mean distance between the internal and the external diameter. The percentage wall thickness (WT %) was calculated by the formula: WT %=2×WT/ED×100%. (38).

Statistics: Data are presented as mean±standard deviation. Student's t test or one-way ANOVA was used to evaluate the statistical significance between two and multiple groups respectively. Differences with p values<0.05 were considered significant.

Results

Plasma MIF concentrations in patients with chronic lung disease: Recent studies have suggested that hypoxia can regulate MIF expression (20, 22) and secretion from endothelial cells (23). Previous studies have shown that the lung can be a major source of MIF released into the systemic circulation (6). The development of pulmonary hypertension in hypoxic states and ventilatory disorders is well recognized (24). The plasma concentration of MIF was examined before and after exercise oximetry in patients with chronic lung disease. Median resting plasma MIF concentrations were higher in patients with mixture alone (1061 pg/ml; range:762-3140), ILD alone (803 pg/ml; range: 292-1845) or ILD plus pulmonary hypertension (1424 pg/ml; range: 519-4396) than in a randomly recruited population-based control group (365 pg/ml; range: 142-4707) that this laboratory has described previously (25). Then the ILD and ILD+PH groups underwent exercise oximetry. In four of five patients in the ILD group, the plasma MIF increased following exercise, but the overall increase was not statistically significant. In all seven individuals of the ILD+PH group the plasma MIF was increased post-exercise and this increase was statistically significant (p=0.02) (FIG. 1).

Figures 2A, 2B:
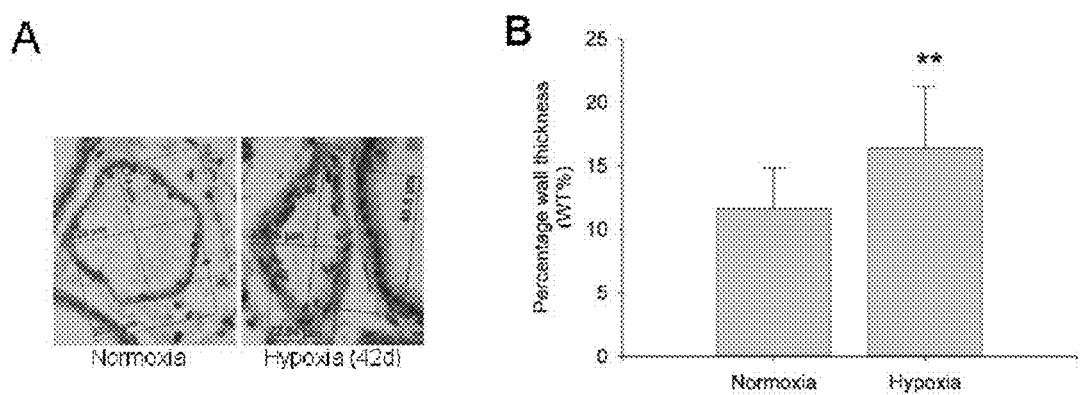
FIGS. 2A-2B: Hypoxia-induced pulmonary vascular remodeling. Mice housed in a 10% normobaric oxygen atmosphere versus normoxic (control) for 42 days demonstrated increased pulmonary vascular cell wall thickness. 2A) histological sections from representative mice were immunostained with α-smooth muscle actin (brown color) to reveal the muscular layer of the vessel wall. External diameter (ED) and internal diameter (ID) of 50 alveolar vessels (with ED of 40 to 100 μm) per animal were determined and recorded, by an independent blinded investigator blinded as to treatment group. Vascular wall thickness was expressed as the percentage of total vessel size (ED). Percent wall thickness (WT %) was calculated as [2×WT]/ED× 100%. 2B) Graphical representation of data from 6 mice per group. The WT % was significantly increased in the hypoxia-treated mice (**p=0.02).
Figures 3A, 3B, 3C, 3D:
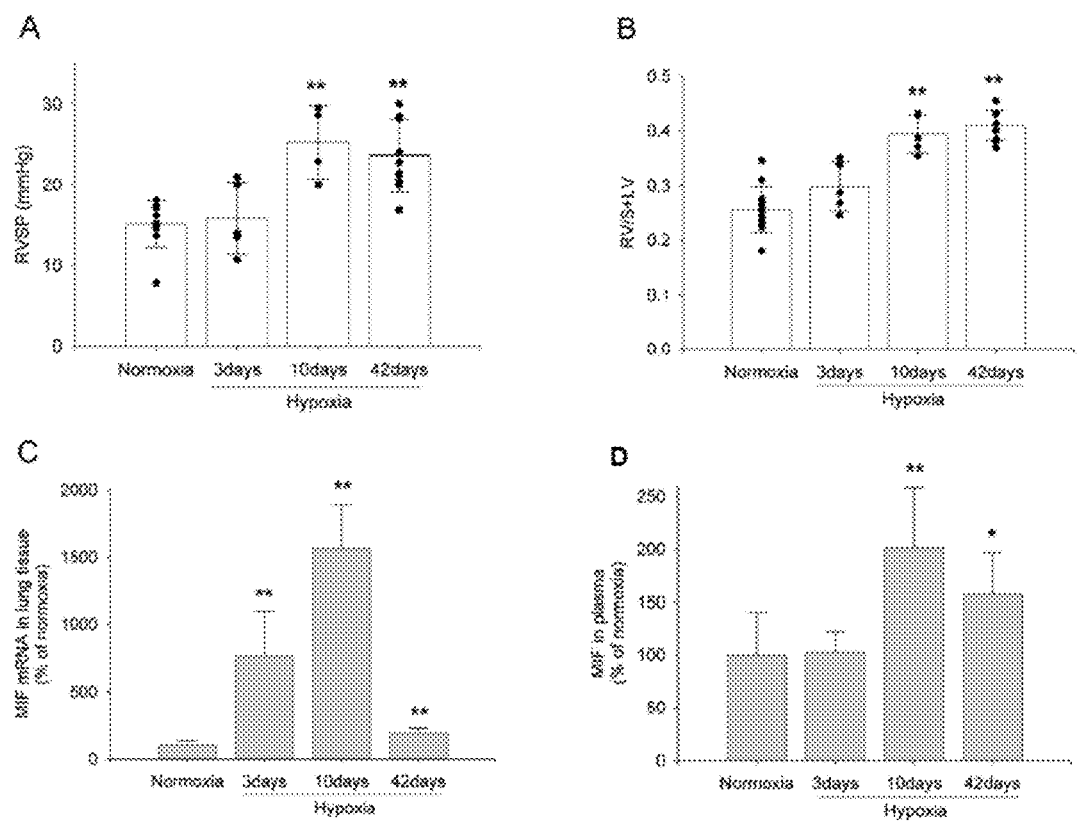
FIGS. 3A-3D: Time-dependent changes induced by hypoxia in a mouse model. Mice housed in either normoxia (control) or 10% normobaric hypoxia for 3, 10, or 42 days. 3A) Right ventricular systolic pressure was measured transdiaphragmatically under isoflurane anesthesia during 100% oxygen inhalation. Chronic hypoxia-induced pulmonary hypertension, characterized by significantly increased right ventricular systolic pressure (RVSP) at 10 and 42 days (25.24±4.57 and 23.56±4.46 mmHg respectively), compared to normoxia controls (15.10±2.91 mmHg)(p<0.01); 3B) The weight of the right ventricle (RV), septum (S), and left ventricle (LV) were measured and RV/S+LV were calculated. Hypoxia resulted in significant right ventricular hypertrophy, represented by significantly increased RV/S+LV ratios (RV/S+LV: hypoxia 10 days: 0.3945±0.039 and 42 days: 0.4101±0.0276, compared to normoxia controls 0.2563±0.0425, p<0.01); 3C) MIF gene expression was measured. MIF mRNA increased in the lung tissue from day 3, peaked at day 10, and stayed at a higher level at least to day 42, (7.6, 15.6, and 1.9 fold increases respectively; ** p<0.01, * p<0.05 vs. normoxia); 3D) MIF protein concentrations in plasma were measured by western blotting. MIF protein concentrations in plasma were also increased at days 10 and 42 days of hypoxia (increased 2.01 and 1.58 fold respectively vs. normoxia, *p<0.05).

MIF expression in a mouse hypoxia model of pulmonary vascular remodeling and hypertension: To investigate the role of MIF in the development of hypoxia-induced pulmonary vascular remodeling and hypertension, a mouse model was used. In this model, male C57BL6 mice were subjected to 10% normobaric hypoxia for up to 42 days. FIG. 2 shows that during the 42 days of exposure there was significant remodeling of pulmonary vasculature as indicated by increased vascular wall thickness, and staining of α-smooth muscle actin within the vessel walls (FIG. 2). To study the relationship between development of pulmonary hypertension and MIF expression, groups of mice were examined after various times of hypoxic exposure (FIG. 3). After 10 days of hypoxia, the right ventricular systolic pressure (RVSP) was significantly increased (FIG. 3A) and this was accompanied by right ventricular hypertrophy (FIG. 3B). The lungs extracted from these animals showed increased levels of mRNA encoding MIF of approximately 7-fold by day 3 of hypoxic exposure, peaking at day 10 (15-fold increase) before declining by 42 days, but remaining around 2-fold higher than baseline (FIG. 3C). The mean plasma MIF concentrations (FIG. 3D) were also significantly increased at days 10 and 42 (2- and 1.5-fold respectively).

Figures 4A, 4B, 4C, 4D, 4E:
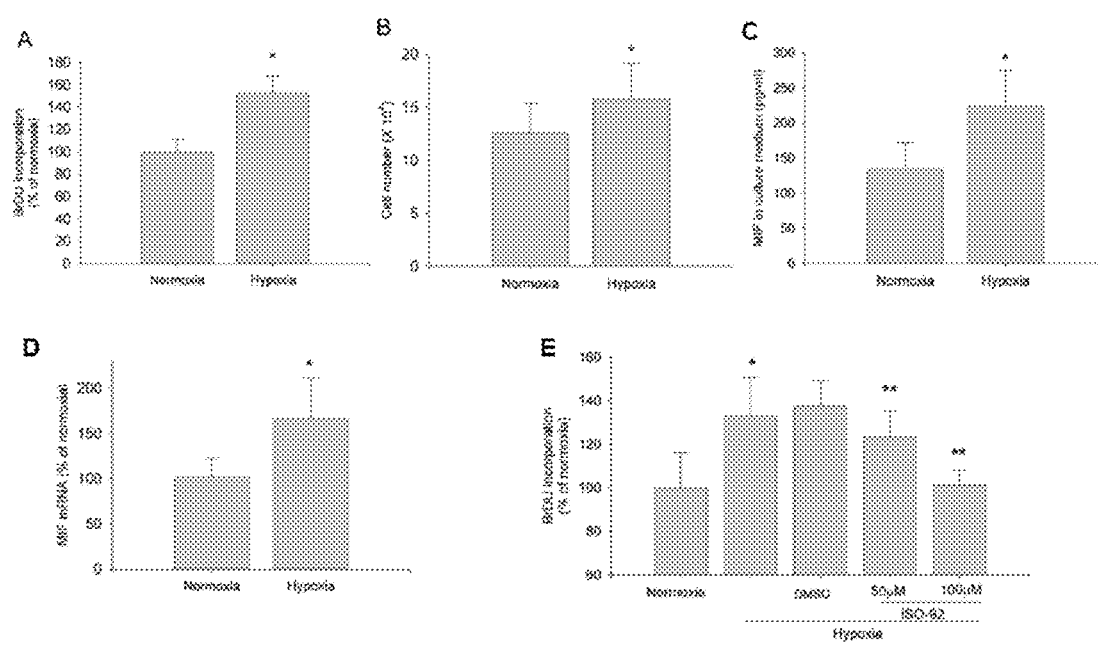
FIGS. 4A-4E: Increased hypoxia-induced cell proliferation in a human lung fibroblast cell line. Human lung fibroblasts (CCL-210) were cultured in normoxia or 1% oxygen atmosphere (hypoxia). After 24 hrs, cell proliferation was evaluated by both BrDU incorporation 4A) and cell enumeration 4B). Cell proliferation in hypoxia was significantly increased (*) compared to growth in normoxia in each evaluation (p=0.001 and 0.03 respectively); The significantly increased growth was associated with increased accumulation of 4C) MIF in the culture medium (p=0.006); and 4D) mRNA encoding MIF in the cells (p=0.008); 4E) ISO-92, but not the vehicle DMSO, inhibited proliferation in a dose-dependent manner (## p=0.04).
Figure 5:
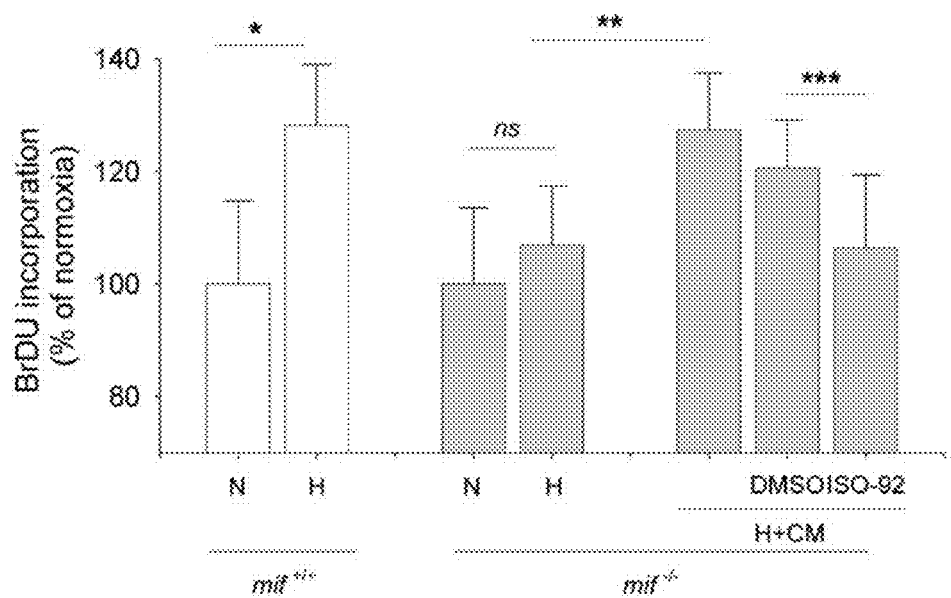
FIG. 5: Increased hypoxia-induced cell proliferation in primary murine lung fibroblasts. Lung fibroblasts were obtained from wildtype (mif+/+) and MIF-deficient mice (mif−/−) mice. mif+/+ cells significantly increased proliferation in 1% oxygen (p=0.004) whereas mif−/− fibroblasts did not. However, mif−/− cells grown in hypoxia and supplemented with conditioned medium (CM) from hypoxic mif+/+ cell cultures increased growth (p=0.006). This increased proliferation was inhibited by ISO-92 (p=0.05), but not the carrier, DMSO.

MIF involvement in fibroblast proliferation in vitro: Pulmonary vascular cell proliferation is the major pathologic change during hypoxia-induced remodeling. The pulmonary vascular wall is composed by three layers of different cells: intimal endothelial cells, medial smooth muscle cells, and adventitial fibroblasts. Hypoxia in vivo induces proliferation of all of these cell types (26), but only fibroblast proliferation is induced by hypoxia in vitro (27). The role of MIF in hypoxia-induced lung fibroblast proliferation was investigated. The effects were examined both in CCL-210 a human cell line (FIG. 4) and in primary mouse lung fibroblasts derived from wild-type (mif+/+) and MIF gene-knockout (mif−/−) mice (FIG. 5). Both BrDU incorporation (FIG. 4A) and absolute cell counts (FIG. 4B) were used to evaluate cell proliferation. Both evaluations showed that there was increased fibroblast proliferation in hypoxia. This was associated with increased accumulation of MIF in the culture medium (FIG. 4C), and increased accumulation of mRNA encoding MIF in the cell lysates (FIG. 4D). To determine if the increased proliferation was due to MIF, MIF activity was inhibited with ISO-92. Hypoxia-induced proliferation was inhibited by ISO-92 in a dose-dependent manner. Measurement of lactate dehydrogenase in the medium of the treated cells showed no significant release of this protein indicating that ISO-92 was not cytotoxic at the concentration used (data not shown).

To further investigate the role of MIF, primary lung fibroblasts were isolated from C57B16 mif+/+ and mif−/− mice. Similar to the human cell line, primary mif+/+fibroblasts increased proliferation in hypoxia (FIG. 5). However, cells from mif−/− mice did not. Furthermore, if the mif−/− cells were incubated with conditioned medium from hypoxia-treated mif+/+ fibroblasts, cell growth significantly increased. This increase in growth was abrogated by the addition of ISO-92 (FIG. 5).

Figures 6A, 6B, 6C:
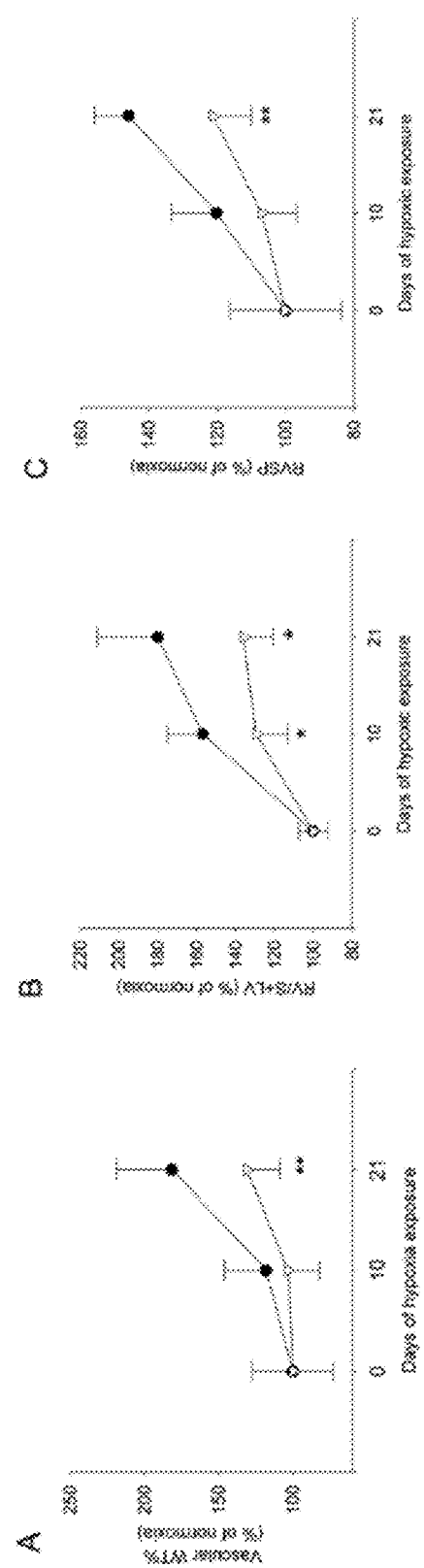
FIGS. 6A-6C: ISO-92 reduction of pulmonary vascular remodeling and hypertension in the mouse hypoxia model. Mice (n=6/group) housed in an atmosphere of 10% oxygen were continuously administered either ISO-92 (1.8 mg/kg/day) or vehicle control via an osmotic delivery device inserted sub-cutaneously on the dorsum of the animal. The animals were then exposed to hypoxia for 10 or 21 days as before Inhibition of MIF significantly reduced all indications of pulmonary vascular remodeling: 6A) vascular wall thickness (VascularWT %), 6B) right ventricle hypertrophy (RV/S+LV), and 6C) right ventricular systolic pressure (RVSP).
Figures 7A, 7B, 7C:
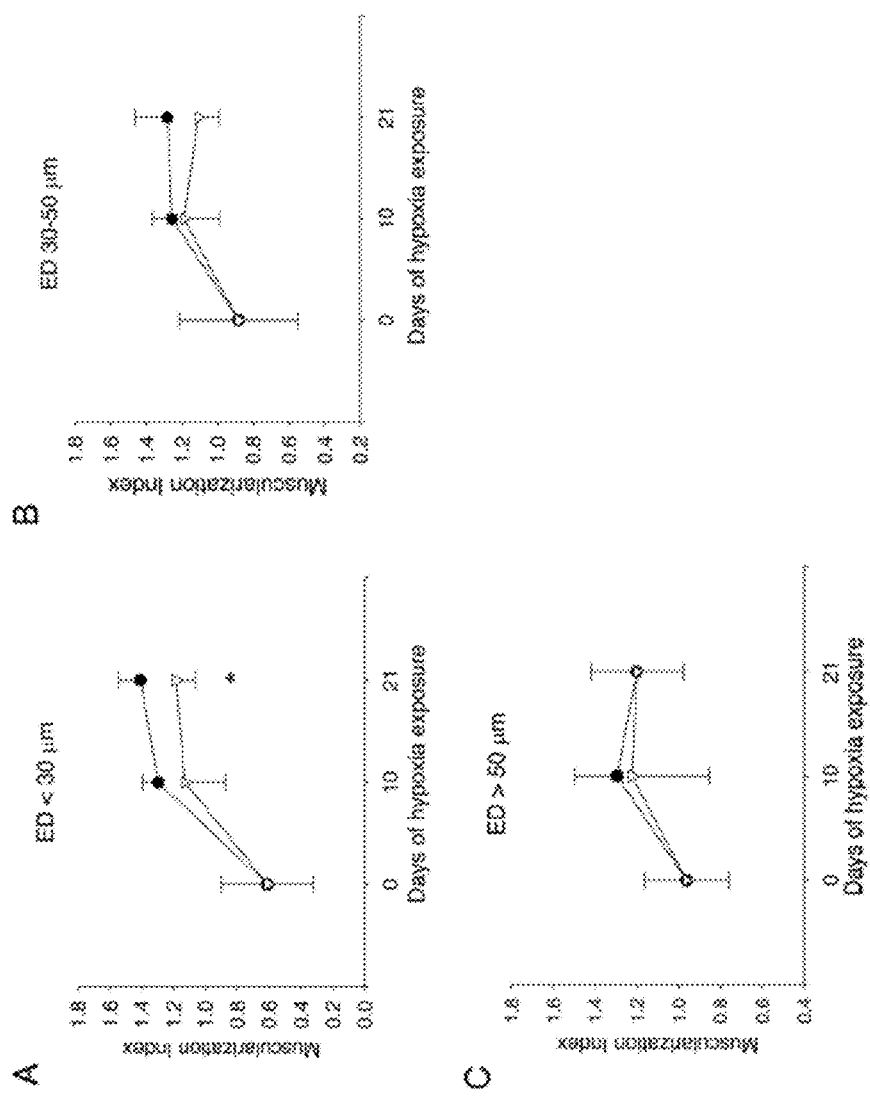
FIGS. 7A-7C: ISO-92 inhibits hypoxia-induced pulmonary vascular muscularization. Muscularization index (MI) was calculated during different hypoxia times and by different treatments (ISO-92 versus vehicle control). ISO-92 significantly inhibited hypoxia-induced vascular muscularization in the small vessel subgroup (ED<30 μm) at 21 d time point. Muscularization index was calculated by MI= (CM number×2+PM number)/total observed vascular number. Data presented as average±SD. *P<0.05 versus vehicle group. Circles—Control; Inverted triangles—ISO-92.

Prevention of pulmonary vascular remodeling and hypertension in the mouse hypoxia model: Since MIF modulated hypoxia-induced fibroblast proliferation in vitro, the effect of inhibiting MIF inflammatory activity on the development of hypoxia-induced pulmonary vascular remodeling and hypertension was examined. Thus, groups of mice were continuously administered either ISO-92 (1.8 mg/kg/day) or vehicle control via an osmotic delivery device inserted sub-cutaneously on the dorsum of the animal. The animals were then exposed to 10% normobaric hypoxia for 10 or 21 days as before. Inhibition of MIF significantly reduced all indicators of pulmonary vascular remodeling and hypertension (RVSP, right ventricle hypertrophy and increased vascular wall thickness—FIG. 6).

Discussion

Pulmonary hypertension (PH) is a common complication of chronic respiratory diseases such as chronic obstructive pulmonary disease (COPD) and interstitial lung diseases (ILD) (28). While the true prevalence of PH in COPD and ILD remains unclear, estimates have suggested that it may occur in up to 80-90% of patients with advanced disease (29-32). In this study, MIF concentrations were examined in human plasma from patients with PH both at baseline and after exercise and used in vitro cell proliferation and development of PH in a mouse model to define the role of MIF in hypoxia-induced pulmonary vascular remodeling and hypertension.

The study of small groups of individuals with chronic lung disease suggests that those with severe chronic lung disease have increased baseline plasma MIF concentrations. Furthermore, those individuals with more severe disease (ILD+PH) increased the plasma MIF after 10 minutes exercise. This suggested that plasma MIF may in part be regulated by tissue oxygenation.

To examine the role of MIF in the development of PH more fully, a mouse model was used in which the animals were subjected to 10%, normobaric hypoxia. These animals underwent significant pulmonary vascular remodeling, significantly increasing the vascular wall thickness over 42 days. The time course study revealed that there were significant increases in RVSP by ten days and this was accompanied by right ventricular hypertrophy. All ventricular pressure measurements were made with the animals breathing 100% oxygen. This was done to ensure that the measurements reflected permanent changes in pulmonary resistance rather than hypoxia-induced constriction. The increases in RVSP and right ventricular weights were associated with increased mRNA encoding MIF in the lung tissue and increased MIF protein in the plasma. This laboratory has previously shown that, under inflammatory conditions such as sepsis, the lungs can be a major source of systemic MIF (6). In this hypoxic study, the level mRNA encoding MIF in the lungs was significantly increased by day 3 of hypoxia and was 15-fold higher than normal at day 10. By 42 days the level had dropped considerably but was still at least double the normoxia level. The plasma level of the MIF protein was increased at 10 and 42 days reflecting the increases in RVSP and cardiac hypertrophy evaluations. This suggests that MIF is involved from the early stages in the pulmonary vascular remodeling events.

Increased cell proliferation and angiogenesis are common adaptive changes to hypoxia. Increased cell proliferation can compensate for the cell death caused by oxygen deprivation, whereas new vascular formation increases the blood flow to a hypoxic area. However, disordered new vascular formation can be pathogenic. In the lung vasculature, uncontrolled cell proliferation and angiogenesis during hypoxia leads to vascular wall thickening, lumen narrowing, increased vascular resistance, and PH. The pulmonary vascular wall is composed by three layers of different cells, the endothelial cells of the intima, the SMCs of the media, and the fibroblasts of the adventitia. Hypoxia in vivo is associated with proliferation of all three cell types. However, fibroblast proliferation takes place earlier after hypoxic exposure than SMCs (26) and in vitro, hypoxia only directly induces fibroblast proliferation, and induces SMC proliferation only when they are in co-culture with fibroblasts (27). Fibroblasts are essential to trigger the vascular remodeling process, which may be due to the fact that they are less differentiated and prepared for localized injury repair (33). Fibroblasts are very plastic, allowing for rapid proliferation, differentiation, and cytokine expression (33). In addition several investigators have suggested that MIF can induce fibroblasts proliferation directly (7, 9-12, 20, 34). Therefore, cultures of lung fibroblasts were chosen, both a human cell line and primary mouse cells, to examine the inter-relationships between hypoxia, MIF and cell proliferation. The data demonstrate that hypoxia induces both MIF expression and proliferation in the fibroblasts, and this was assessed by BrdU incorporation and confirmed by cell counts using a hemocytometer. These results are consistent with the findings of others regarding MIF production and hypoxia-induced fibroblast proliferation (20).

It has also been demonstrated here, however, that molecular inhibition of MIF, by administration of an MIF inhibitor such as the small molecule inhibitor ISO-92, can block hypoxic cell proliferation, which indicates that MIF is a key mediator of fibroblast proliferation under hypoxic conditions. In the current study two different ways were used to show the critical role of MIF. The first was to use the MIF-specific inhibitor, ISO-92, a small synthetic molecule with high affinity for MIF developed by rational design to fit into the hydrophobic active site of MIF (35). ISO-92, but not the vehicle control, DMSO, was able to inhibit hypoxia-driven proliferation in CCL-210 cells. Treatment of the cells with 100 µM ISO-92 had no effect on the growth of cells cultured in normoxic conditions, nor did it cause accumulation of lactate dehydrogenase in the culture medium (data not shown). These data indicate that ISO-92 did not inhibit cell proliferation by cytotoxic effects, and that hypoxia induces the accumulation in the culture medium of a material (MIF) that then acts in an autocrine manner to stimulate proliferation. To further establish the role of MIF in fibroblast proliferation, primary cell lines were established from wild-type and MIF-deficient mice. These studies revealed that while mif+/+ fibroblasts increased proliferation in hypoxia, mif−/− did not indicating that inhibitors of MIF by any MIF inhibitor can have therapeutic benefit in the setting of hypoxia. However, conditioned medium from mif+/+ fibroblasts grown under hypoxic conditions was able to induce increased proliferation in mif−/− cells cultured in hypoxia. This increased proliferation was inhibitable by ISO-92. It should be noted that conditioned medium alone was not sufficient to induce mif−/− cell proliferation. Increased cell proliferation occurred only when conditioned medium from hypoxic mif+/+ cells was combined with hypoxic conditions in the mif−/− cells. This finding suggests that there is a hypoxic priming of the cells which are then responsive to MIF stimulation.

As a final illustration of proof of concept that MIF is involved in the hypoxia-induced pulmonary vascular remodeling and hypertension, ISO-92 (or vehicle control) was administered to mice housed under hypoxic conditions. Molecular inhibition of the MIF inflammatory site by administration of the small molecule MIF inhibitor ISO-92 significantly reduced vascular remodeling and right ventricular hypertrophy. The overall benefit being the reduction of right ventricular systolic pressures by approximately 53% at 21 days (normoxia: 13.8±2.3 vehicle: 20.2±1.4 ISO-92: 16.8±1.5 mm Hg). The administration conditions used were such that the drug delivery pump was inserted prior to hypoxic exposure to avoid animals experiencing multiple changes in oxygen tension that would occur with a surgery post-initiation of hypoxia. In addition, a concentration of ISO-92 was used that was derived from the in vitro cell culture studies outlined above, and calculations of how similar concentrations may be achieved in vivo.

Overall, the results show a key role for MIF in the development of hypoxia-induced pathologies including, particularly, pulmonary vascular remodeling and hypertension. Since baseline plasma MIF is increased in individuals with interstitial lung disease and pulmonary hypertension, and can further increased on exercise, MIF is a useful biomarker in the diagnosis and treatment of hypoxia-driven pulmonary hypertension. Perhaps more importantly, the data show that inhibition of MIF inflammatory activity is a useful treatment strategy to inhibit the development and progression of hypoxia-induced vascular remodeling and the devastating consequences of the development of pulmonary hypertension.

CNS Hypoxia

Hypoxic conditions affecting the central nervous system can occur in a variety of areas of life. Hypoxic conditions occur, for example, at high altitude, during closed circuit underwater breathing and during mask-on hypoxia training. Clinically relevant situations associated with hypoxia include severe head trauma, and chronic lung diseases such as interstitial lung disease (ILD) and chronic obstructive pulmonary disease (COPD). Recent studies have shown that pulmonary function is significantly related to information processing speed and fine motor dexterity, and that decreased lung function (associated with hypoxia) is related to poorer cognitive function and increased subcortical atrophy in mid-adult life. Hypoxia causes regional changes in the brain including neurogenesis, hippocampal atrophy, transcription factor regulation, and altered protein expression. These changes are associated with impaired sleep quality, mental performance, productivity, and general well-being. Inflammatory processes may substantially contribute to the cerebral pathology.

Studies in an animal model disclosed herein indicate that inhibition of MIF during hypoxia reduces both metabolic and oxidative changes in the brain. A previously unknown role for MIF in hypoxia-induced cognitive and memory dysfunctions is examined and alleviation of hypoxia-induced spatial memory defects by MIF inhibition is disclosed. Hypoxia-associated changes in cognition and memory and their relation to oxidative stress and altered gene expression in the regions of interest are identified. Mice are subjected to a battery of standard tests to evaluate the effects of various periods of hypoxia on anxiety, recognition, spatial memory and emotion. Post-assessment, the animals are euthanized and the brain tissue collected and assessed for oxidative changes and altered gene expression. Specific inhibition of MIF is employed to prevent or attenuate hypoxia-associated pathogenesis, and particularly, deleterious changes in cognition or memory.

Materials and Methods

MicroPET scanning: MicroPET scanning can be conducted using an appropriate system, such as Siemen's Inveon. The Inveon is a dedicated small animal positron emission tomography (PET) scanner housed in the Feinstein Institute for Medical Research. This scanner is an ultra-high resolution tomography that includes a built-in transmission source used for the quantitative assessment of radiotracer binding. The use of $^{18}$FDG is preferred.

Scanning methods: All animals being scanned are housed in the Center for Comparative Physiology, within the Feinstein Institute. Animals receive an intraperitoneal (i.p.) injection of $^{18}$FDG (between 1-2 mCi). Following a 45-minute uptake period, during which time the animals are awake and freely moving, they are anesthetized using ketamine/xylazine (100 mg/kg ketamine with 10% xylazine; Fort Dodge). Animals are placed into a stereotaxic frame designed and constructed specifically for the Inveon. Once in position, they are scanned for 20 minutes. Absolute and relative metabolic values for each animal's post-treatment scans are obtained using Pixel-wise modeling software (PMOD). These scans are compared to their initial baseline scan using averaged $^{18}$FDG uptake within regions of interest divided by the whole brain $^{18}$FDG activity. Significant differences in absolute and region-of-interest to whole-brain relative metabolic glucose uptake are analyzed using student t-tests and repeated measures ANOVA.

Irwin observational screen. The integrity of sensory and motor systems can be assessed with valid and reliable tests that have already been published (39). A behavioral screen that consists of a total of 48 separate measurements is recorded for each mouse. Assessment starts with observation in a cylindrical glass flask (height 15 cm, diameter 11 cm) followed by transfer to an arena (55×33 cm). These observations are continued with manipulations using tail suspension for measuring visual acuity, grip strength, body tone, and reflexes. Subsequently, the mouse is restrained in a supine position to record autonomic responses, skin color, limb tone, and abdominal tone. Salivation and provoked biting are also be recorded. Measuring the righting reflex and negative geotaxis completes the screen. Throughout the procedure, instances of abnormal behavior, irritability, and vocalizations are recorded.

Rotarod task. This task measures motor balance that depends on the cerebellum and motor cortex (40). Mice are subjected to the accelerating rotarod test. Each mouse is placed in a rotating drum (ENV-576M, Med Associates Inc, St. George, Vt.), which is accelerated from 4 to 40 rpm over the course of 5 min. The time at which each animal falls from the drum is recorded. A mouse receives 3 consecutive trials and the longest time on the drum is used for analysis.

Morris water maze tasks. Spatial memory is assessed using two tasks in the Morris water maze, a standard task that measures spatial reference memory (41, 39), and a training-to-criterion task that measures memory flexibility and new learning (42). The second task is exquisitely sensitive to disruptions of the hippocampus. The apparatus consists of a circular pool (160 cm diameter, opaque water at 20° C.±1° C.) surrounded by prominent distally located visual cues. Each mouse is placed into the water facing the sidewalls and will be allowed to swim until it finds the hidden platform (top surface 1.5 cm below water level). The maximum trial duration is 90 sec, with 20 sec on the platform at the end of the trials. Swim paths are monitored by a videotracking system (AnyMaze, Stoelting). For the reference memory task, mice are trained to find the platform that is always in the same location in the pool. The task is divided into two phases: in the first phase, mice are trained to find a "large" hidden platform (diameter, 24 cm) for 12 trials (4 trials per day). After this, a first probe trial will be performed: each mouse swims for 60 sec with the platform removed from the pool. The second phase consists of 24 trials, in which the mice find a "small" platform (diameter, 16 cm). A second probe trial will occur at the end of training. For the training-to-criterion task, mice are required to find the platform, placed in 5 consecutive locations in the water maze. Each animal is trained, for up to 8 trials per day, to a performance criterion of three successive trials with an escape latency of less than 20 sec before being transferred to the next location on the next day (maximum trials will be 32 for each location).

Novel object recognition task. Recognition memory that depends on the temporal (rhinal) areas of the cerebral cortex (43) is assessed. Two-object recognition memory is tested in a chamber (25 cm long, 25 cm wide, 60 cm high) with an open ceiling, constructed of white plastic. It is be illuminated from the top by a 40W white bulb. A camera is mounted on top and is attached to a video tracking system (Ethovision, Noldus) that tracks the behavior. The floor is covered with a layer of bedding. Before formal testing, each mouse is familiarized with the empty chamber for 3 sessions (5 min each over a period of 2 days). A single trial consists of 3 phases: sample, delay, and choice. For the sample phase, mice are placed in the chamber and allowed to explore two identical objects for a period of 5 min. For the delay phase, mice are placed in their home cage for 10 min. During this interval, test objects will replace sample objects. One of them is identical to those in the sample phase ("familiar object") whereas the other are different ("novel object"). Extreme care is taken to place the objects in exactly the same positions occupied by the sample objects in phase one of the test. For the choice phase, mice are allowed to explore for 5 min. Object exploration is scored when the mouse touches the object with the face (mouth, whiskers, and nose). Touching the object with any other part of the body while facing another direction is not be counted as exploration. After the experiment, videotapes of the trials are reviewed and the time (in sec) spent on each of the objects is obtained. A1 and A2 are defined as the times exploring the sample objects, A3 as the time exploring the familiar object, and B1 as the time exploring the novel object. To determine recognition memory, the exploration ratio is measured in the sample phase (run 1) which is defined as $[(A1+A2)/300]$, the exploration ratio in the test phase (run 2) is defined as $[(A3+B1)/300]$, the preference index is defined as $[B1-A3]$, and the discrimination ratio is defined as $[(B1-A3)/(B1+A3)]$.

Elevated plus maze task. The elevated plus maze consists in two open arms and two closed arms (44). Each mouse is placed at the end of an open arm and is allowed to explore the maze for 5 min. Well-adapted mice explore the open and closed arms relatively equally, but maladapted mice fail to explore the open arms and spend time predominately in the closed arms.

Open field task. The open field consists of a circular arena (50 cm diameter) made of matt white perspex with walls 30 cm high. The mice are placed in the center of the arena at the start of the 10-min test period and their movement around the arena is recorded using a videotracking system (Ethovision, Noldus) (45). The parameters to record are total distance travelled, time spent active, percentage of the test time spent in the central part of the arena and defecation. The open field is thoroughly cleaned using Amphiset 80™ and dried prior to the next mouse. The maze is illuminated by normal room lighting (fluorescent strip lighting approximately 1.5 m above the maze) and by three lamps (red bulbs, approximately 1-1.5 m away from the maze) providing diffuse illumination.

Fear conditioning. Mice are tested in a fear-conditioning paradigm, which is an example of classical Pavlovian conditioning that depends on the amygdala (46). The paradigm consists of pairing a tone (the conditioned stimulus, CS) with an electric shock (the unconditioned stimulus, US) delivered on the footpad. Mice learn to associate the tone-CS with the shock-US and thereafter freeze in anticipation of the shock after hearing the tone, thus displaying auditory conditioning. Moreover, mice also learn to associate the context in which they receive the noxious stimulus (i.e., the context becomes a CS) and will thereafter freeze when placed in the environment in which they were shocked, thus displaying context conditioning. Studies using this paradigm have determined that the amygdalar circuit and the auditory inputs to the amygdala are required for the execution of this task of emotional memory (47). Mice with a damaged amygdala fail to exhibit appropriate freezing during auditory and contextual conditioning. For implementation of the fear-conditioning paradigm, two chambers are used: a conditioning chamber and a testing chamber. The first chamber is a transparent Plexiglass shock chamber (18×18×30 cm3), equipped with a stainless steel grid floor (diameter of each grid: 0.5 cm, spacing: 0.5 cm; Precision regulated animal shocker, Coulbourn Instruments), which will be dimly lit and enclosed within a sound-attenuating chamber. The testing chamber is another distinct Plexiglas chamber (lab-made) to minimize generalization from the conditioning environment. This second chamber will be brightly lit and will contain a black Formica floor that will be washed with peppermint soap. A video camera will be mounted at the top of the chambers allowing videotaping during auditory fear testing for later scoring. The software package FreezeFrame (Actimetrics) can be used for delivering the conditioning protocols and for automated scoring of movement and freezing. Testing for contextual conditioning takes place in the conditioning chamber. The fear conditioning procedure occurs as follows: on the day before conditioning (day 1), mice are habituated to the training and testing chambers for a minimum of 10-15 min. Habituation is counterbalanced between groups to control for possible order effects. On the day of conditioning (day 2), mice are given 3 min to acclimate to the conditioning chamber. This is followed by the presentation of five pairings of a 20-sec tone-CS (5 kHz, 75 dB) that will coterminate with a foot shock-US (0.5 sec, 0.5 mA). The intertrial interval is varied pseudo-randomly between 90 and 120 sec. After conditioning, mice will be returned to their home cages. On the day of testing (day 3), the fear responses conditioned to the tone-CS and the conditioning apparatus (context-CS) is tested separately. Responses conditioned to the tone-CS are measured in the testing chamber. After a brief acclimation period to the test chamber, the mice receive two test tones (20 sec, 5 kHz, 75 dB; interval, 100 sec). Then, they are placed in the conditioning chamber and allowed to explore for 3 min (to give them time to recognize the context), after which the duration of freezing is measured for 5 min. Right after this "silent" period, the mouse is exposed to 20 trials of tone-CS alone (20 sec) within the chamber, with an inter-trial interval of 120 sec. To determine the extinction of the fear response (48) the amount of freezing during each tone presentation is measured.

Clock maze: A navigational test is used to measure spatial working memory, modified from Deacon and Rawlins (2002). The apparatus (termed "clock maze") is a circular base platform (diameter, 85 cm) surrounded by a clear wall (30 cm high), sealed to the base by aquarium sealant to make it waterproof Cold water (20° C.±1° C.) is added to a depth of 2 cm, sufficient to wet the underside of the belly of mice. The perimeter wall is pierced by 12 holes, 4 cm in diameter, arranged equidistantly around the circumference so that they are 23 cm apart. The lower edge of each hole is 3 cm above the maze floor, that is, at mouse head level. Eleven of these tubes were sealed with black plugs, flush with the internal pool wall surface; one is open and led to an escape pipe, which is 4 cm in diameter, made of black flexible plastic. Thus, from within the clock maze, the true exit looks similar to the decoys, even to the human eye. The pool is surrounded by distal unmoving cues which are illuminated by focal white lights within a darkened testing room. Besides the clock maze, there is a pre-training box (28 cm long×8 cm wide×30 cm high), which is made of black wood, open on the top and with one short side (made of an acrylic sheet) containing an escape tube of black plastic (diameter, 4 cm, length, 4 cm), with its lower edge at 3 cm above the base, at mouse head height. The escape pipe, as used on the clock maze, was fitted onto the tube. There was also a pre-training tunnel (rectangle, 39 cm long×24 cm wide×30 cm high), made of clear plastic, and is filled with water to 2.5 cm and has 2 black plastic escape tubes set in diagonally opposite corners of the short sides, centered 5 cm above the base and 5 cm from the adjacent longer wall. One tube is open and leads to the escape pipe, while the other is sealed with a black plug. For each apparatus, the task is to escape into the open tube and connected pipe; the pipe is then removed and the mouse was transported to the nearby home cage. For pre-training, each mouse is first placed in the far end of the pre-training box to learn the principle of escaping into the tube. The mice receive 4 trials in one day with each trial lasting a maximum of 60 sec. The next day, mice receive 4 trials in the pre-training tunnel. The animal is placed facing one of the long sides in a semi-random fashion (not more than 3 consecutive times the same way) and the time taken to enter the open tube was recorded by software (Ethovision). Errors are defined as approaching the closed tube (within a head's length). Maximum trial length is 60 sec. For the working memory task, a mouse undergoes 4 trials per day in the clock maze for 3 consecutive days. The target remains in a fixed location during the initial 4 trials, but is switched to a different location during the next 4 trials, and yet another location for the final 4 trials. Therefore, each mouse is required to learn 3 different targets during the test. The latency to reach the target is recorded by software (Ethovision) with a maximum of 60 sec for each trial.

Immediately post behavioral assessment, the animals are divided into two sets; one set is subjected to electrophysiological studies while the other set has their brain tissue collected and assessed for oxidative changes and altered gene expression, including inflammatory mediators and genes associated with synaptic plasticity (49).

CNS Results I

MIF is associated with two enzymatic activities. One, a tautomerase, lies in a hydrophobic cavity formed between two adjacent subunits of the homotrimer (50) for which the physiological function or substrate is still unknown. This hydrophobic cavity has been identified as the inflammatory active site of the molecule (51). Blocking of this active site inhibits MIF binding to its receptor CD74, inhibits MIF-derived inflammatory activity (55) and significantly improves survival in animal models of sepsis (51-53) Recently, the thyroid hormone thyroxine has been identified as a natural inhibitor of MIF inflammatory activity (54).

In hypoxia studies discussed hereinabove, it has been found that blocking the inflammatory sites of MIF prevents pulmonary vascular remodeling and hypertension. In these studies, groups of mice were continuously administered either ISO-92 (1.8 mg/kg/day) or vehicle control via an osmotic delivery device inserted subcutaneously on the dorsum of the animal. The animals were then exposed to 10% normobaric hypoxia for 10 or 21 days as before Inhibition of MIF significantly reduced all indications of pulmonary vascular remodeling and hypertension including increased vascular wall thickness, right ventricle hypertrophy and right ventricular systolic pressures (RVSP).

Figure 8:
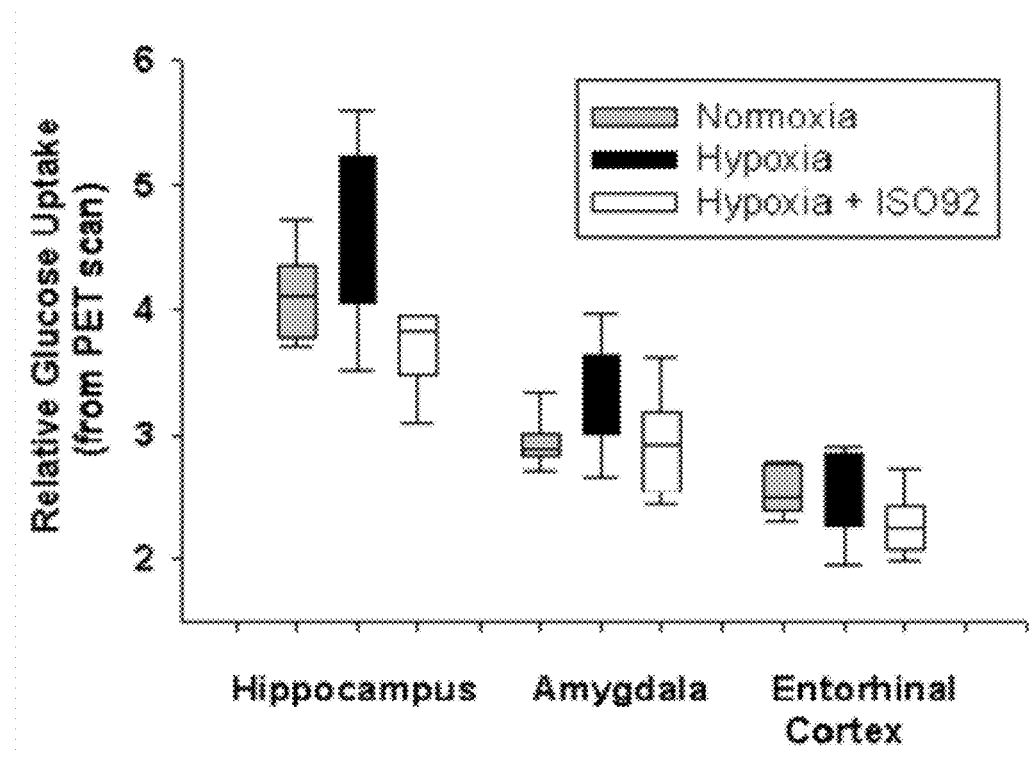
FIG. 8: Graphical semi-quantitation of $^{18}$F-FDG uptake in mouse brains in normoxia or 10% hypoxia as revealed by microPET imaging.

Further developing these studies, it is herein disclosed that inhibition of MIF prevented altered 2-deoxy-2-($^{18}$F) fluoro-D-glucose ($^{18}$F-FDG) uptake in the brain of hypoxic mice (FIG. 8). Small-animal PET provides the opportunity to image brain activation before and after periods of hypoxia. The technique assumes that changes in $^{18}$F-FDG uptake or metabolism reflect altered metabolic demand secondary to changes in neuron firing. In this way, regional changes in brain $^{18}$F-FDG uptake can reflect changes in brain function. In this study, a standardized uptake value (SUV) (56) was used, a simple semi-quantitative index, calculated by measuring the activity concentration in a region of interest (ROI) during a short-duration (10 min) static scan acquired 60 min after injection and then normalized for the injected dose or weight of the animal. In the current study, mice (n=5/group) underwent hypoxia for ten days in the presence or absence of MIF inhibition with ISO-92 as described above. Averaged coronal images through the mouse brain were obtained from each group. $^{18}$FDG images demonstrated that hypoxia produced a marked increase in brain glucose metabolism (Hypoxia 10 days) compared to baseline values (Normoxia). However, in the presence of the MIF inhibitor, ISO-92, these increases were blocked completely (Hypoxia 10 days+ISO-92). Semi-quantitative analysis of specific brain regions from these results is shown in FIG. 8. While none of the differences between the groups reached statistical significance, the median value of the MIF inhibitor group was lower in each case, and it suggests that with a larger group size, statistical significance would be achieved. PET scan data is assessed in conjunction with quantitative gene and protein expression analysis, evaluation of oxidative stress, electrophysiological and behavior studies.

CNS Results II

The behavioral and cognition tests hereinabove described are performed on animals subject to (i) normal oxygen conditions, (ii) hypoxic conditions, and (iii) hypoxic conditions but with the animal treated with an MIF inhibitor, such as ISO-92. The effect of the MIF inhibitor on any hypoxia-induced impairment is assessed.

Behavioral Assessment: All testing occurred between 10:00 and 18:00 h and the mice were between 8-12 weeks old. Each mouse was subjected to a four-stage assessment consisting of a primary screen, adapted from Irwin (1968) and the first stage of the SHIRPA procedure (Rogers et al. 1997), an open-field test that measured spontaneous locomotion (Contet et al. 2001), a rotorod test that measured motor coordination (Contet et al. 2001), and a navigational test that measured spatial working memory, modified from Deacon and Rawlins (2002). Each of these tests was separated by at least 1 day.

The primary screen started with anatomical parameters (coat length, hair length and hair morphology), followed by observation in a cylindrical glass flask (height 15 cm, diameter 11 cm), which measured body position, spontaneous activity, respiratory rate, tremor occurrence, defecation, and urination. Transfer to an arena (55 cm×33 cm) allowed for measuring of transfer arousal, latency to move in the arena, and locomotion in the arena. This was continued with manipulations for measuring piloerection, palpebral closure, startle response, gait, pelvic elevation, tail elevation, touch escape, positional passivity, trunk curl, limb grasping, visual placing, grip strength, body tone, pinna reflex, corneal reflex, toe pinch, body length, tail length, lacrimation, whisker morphology, provoked biting, salivation, heart rate, abdominal tone, skin color, and limb tone. Measuring several reflexes (wire maneuver, righting reflex, contact righting, negative geotaxis) completed the screen. Throughout the screen, incidences of fear to the experimenter, irritability, aggressivity to the experimenter, vocalizations, and abnormal behavior were recorded. Finally, body weight was measured. The observed parameters were grouped according to five functional categories, which were muscle and spinal function, spino-cerebellar function, sensory function, neuropsychiatric function, and autonomic function (Rogers et al. 1997). The summed scores for each function were averaged across mice with similar treatment and these were then subjected to statistical analysis.

For the open-field test, each mouse was placed in an empty chamber (30 cm×50 cm) with 15-cm high walls made of opaque white acrylic for 1 min under dim red light. Movement was recorded from a centrally-placed video camera using automated video tracking software to record the distance traveled (Ethovision, Noldus).

For the rotorod test, mice were placed individually on a rotating drum (ENV-576M, Med Associates Inc, St. George, Vt.), which accelerated from 4 to 40 rpm over a course of 5 min. The time at which the mouse fell off the drum was recorded. The test was repeated 5 times for each mouse with an interval of at least 1 h between trials. The room was illuminated with low-level white lights.

The navigational test that measured spatial working memory was modified from Deacon and Rawlins (2002). The apparatus (termed "clock maze") was a circular base platform (diameter, 85 cm) surrounded by a clear wall (30 cm high), sealed to the base by aquarium sealant to make it waterproof. Cold water (20° C.±1° C.) was added to a depth of 2 cm, sufficient to wet the underside of the belly of mice. The perimeter wall was pierced by 12 holes, 4 cm in diameter, arranged equidistantly around the circumference so that they were 23 cm apart, like the 12 h on a clock face. The lower edge of each hole was 3 cm above the maze floor, that is, at mouse head level. Eleven of these tubes were sealed with black plugs, flush with the internal pool wall surface; one was open and led to an escape pipe, which was 4 cm in diameter, made of black flexible plastic. Thus, from within the clock maze, the true exit looked similar to the decoys, even to the human eye. The pool was surrounded by distal unmoving cues (face masks, large curtain, a bench), which were illuminated by focal white lights within a darkened testing room. Besides the clock maze, there was a pre-training box (28 cm long×8 cm wide×30 cm high), which was made of black wood, open on the top and with one short side (made of an acrylic sheet) containing an escape tube of black plastic (diameter, 4 cm, length, 4 cm), with its lower edge at 3 cm above the base, at mouse head height. The escape pipe, as used on the clock maze, was fitted onto the tube. There was also a pre-training tunnel (rectangle, 39 cm long×24 cm wide×30 cm high), made of clear plastic, and was filled with water to 2.5 cm. It had 2 black plastic escape tubes set in diagonally opposite corners of the short sides, centered 5 cm above the base and 5 cm from the adjacent longer wall. One tube was open and leads to the escape pipe, while the other was sealed with a black plug. For each apparatus, the task was to escape into the open tube and connected pipe; the pipe was then removed and the mouse was transported to the nearby home cage. For pre-training, each mouse was first placed in the far end of the pre-training box to learn the principle of escaping into the tube. The mice received 4 trials in one day with each trial lasting a maximum of 60 sec. The next day, mice received 4 trials in the pre-training tunnel. The animal was placed facing one of the long sides in a semi-random fashion (not more than 3 consecutive times the same way) and the time taken to enter the open tube was recorded by software (Ethovision). Errors were defined as approaching the closed tube (within a head's length). Maximum trial length was 60 sec. For the working memory task, a mouse underwent 4 trials per day in the clock maze for 3 consecutive days. The target remained in a fixed location during the initial 4 trials, but it was switched to a different location during the next 4 trials, and yet another location for the final 4 trials. Therefore, each mouse was required to learn 3 different targets during the test. The latency to reach the target was recorded by software (Ethovision) with a maximum of 60 sec for each trial.

Figure 11:
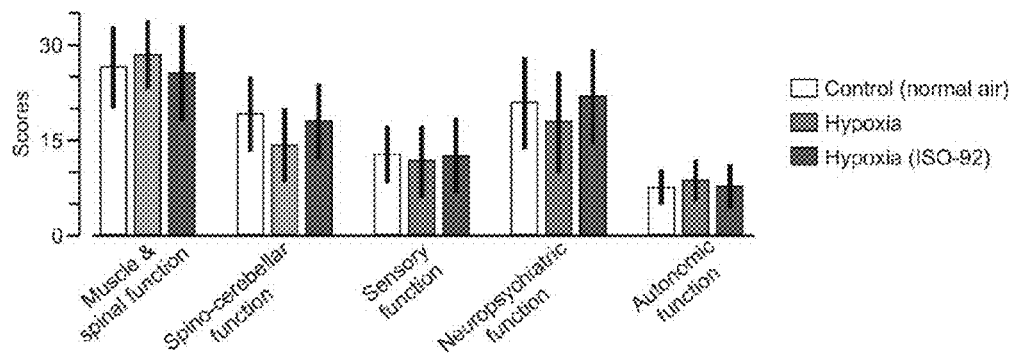
FIG. 11: Behavioral testing results. The control group (n=5) experienced normal air conditions during the experiment and displayed the expected performance in each of the 4 tests, allowing for comparison with the other groups. The hypoxia group (n=5) was exposed to 10 days of 10% oxygen (in a hypobaric chamber) before undergoing testing. The animals were also maintained in the hypobaric chamber for the duration of the behavioral assessment. Hypoxic mice performed similarly to the control group in the observational screen (test 1), the rotorod (test 2) and the open field (test 3). However, they were clearly impaired in the clock maze task that measured working memory (test 4), displaying much longer latencies to find the target as the test progressed.
Figure 11:
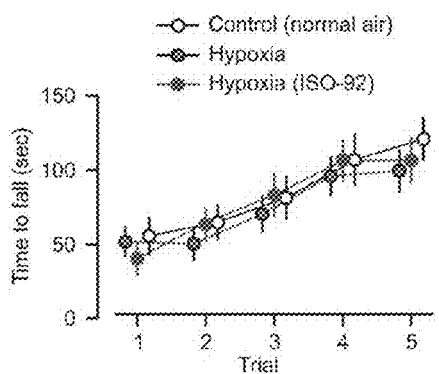
Figure 11:
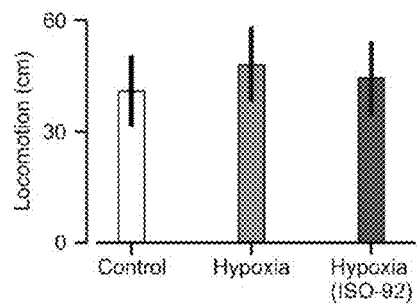
Figure 11:
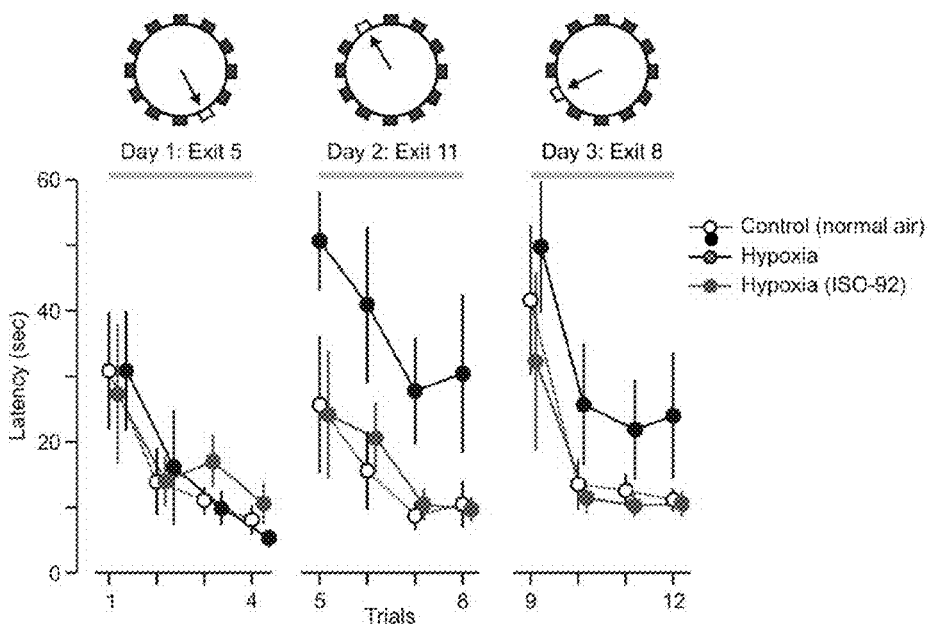

FIG. 11 shows the results for the initial set of mice. The control group (n=5) experienced normal air conditions during the experiment and displayed the expected performance in each of the 4 tests, allowing for comparison with the other groups. The hypoxia group (n=5) was exposed to 10 days of 10% oxygen (in a hypobaric chamber) before undergoing testing. The animals were also maintained in the hypobaric chamber for the duration of the behavioral assessment. Hypoxic mice performed similarly to the control group in the observational screen (test 1), the rotorod (test 2) and the open field (test 3). However, they were clearly impaired in the clock maze task that measured working memory (test 4), displaying much longer latencies to find the target as the test progressed. This result is consistent with the brain system responsible for encoding working memory as being affected by the prolonged exposure to hypoxia.

Crucially, a third set of mice (n=4) that underwent hypoxia but had the MIF inhibitor ISO-92 delivered to the dorsal hippocampus (via osmotic pumps) showed completely normal performance in the clock maze task, showing that MIF inhibitors, such as ISO-92, are capable of protecting the brain from the deleterious effects of hypoxia.

Figure 9:
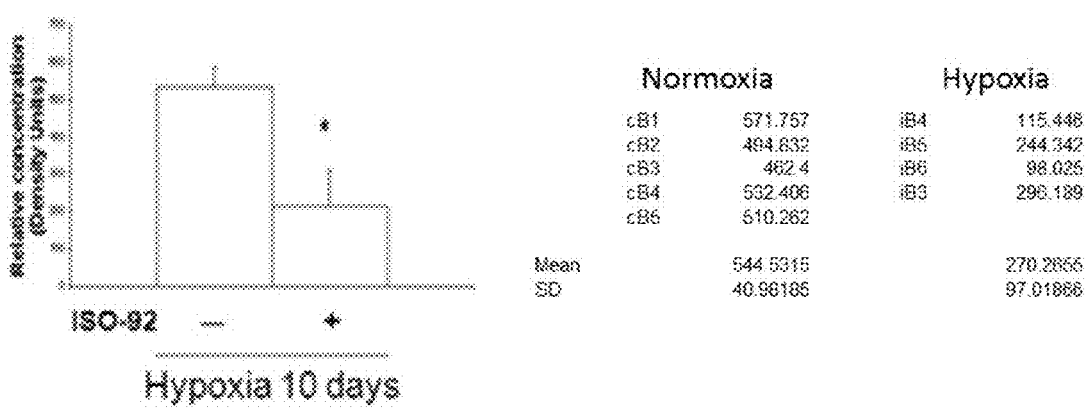
FIG. 9: Protein carbonyls in brain after 10 days hypoxia.

MIF and oxidative stress: To examine the effects of MIF inhibition on the oxidation of proteins in the brain, the brains of mice that had undergone 10 days of 10% normobaric hypoxia (see FIG. 8) were examined Dithiothreitiol (DTT; 25 mM final) was added immediately to an aliquot of the cell homogenate to prevent oxidation. Protein carbonylation was assessed by reacting with 2,4-dinitrophenylhydrazone (DNPH) as described previously (57). Oxidized proteins were identified by immuno-detection of the DNPH-derivatized carbonyl groups in proteins (2.5 µg) that had been separated by 10% SDS-PAGE and transferred to a nitrocellulose membrane (FIG. 9). Immuno-reactive protein bands were detected using chemiluminescence exposure of X-ray film, and proteins were quantified using laser-scanning densitometry. The data show that inhibition of the MIF inflammatory active site during hypoxia significantly reduces protein oxidation in the brain.

Figure 10:
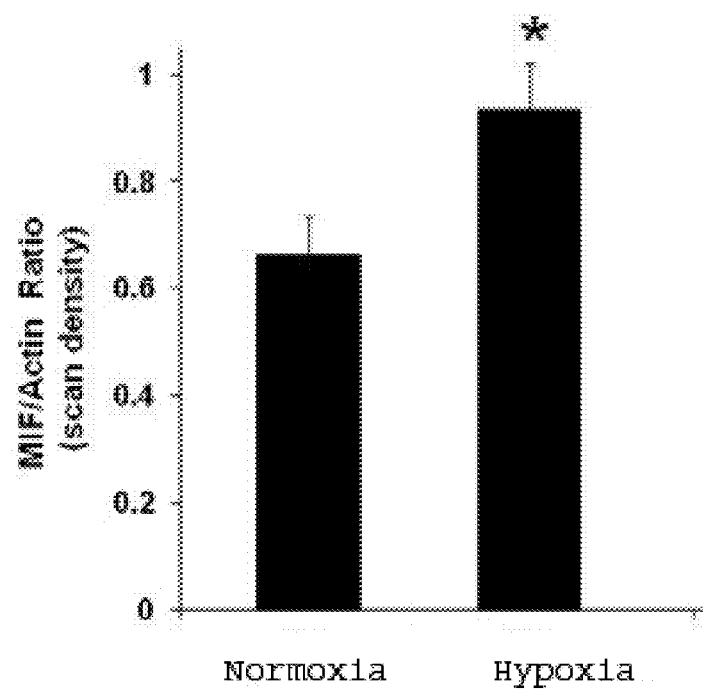
FIG. 10: MIF accumulation in brain tissue is significantly increased (p<0.05) after 10 days normobaric 10% hypoxia.

Hypoxia causes regional changes in protein expression in the brain (58). It was explored whether MIF plays an important role in the cognitive and mnemonic dysfunctions associated with hypoxia. MIF levels were examined in brain tissue before and after 10 days of exposure to 10% hypoxia. Under these conditions, MIF accumulates in significantly increased amounts in the brain tissue, see FIG. 10, including in the amygdala and hippocampus.

Electrophysiology studies. Studies are initially focused on the hippocampus because: i) studies by applicants have identified hypoxia associated changes in metabolism and mRNA elaboration in the hippocampus; ii) pyramidal cells in the CA3 field and granule cells in the dentate gyms show positive immunostaining for MIF (59-61); iii) MIF expression parallels hippocampal cell proliferation during stress (62); iv) MIF is recognized as a pro-inflammatory counter-regulator of the anti-inflammatory activities of the glucocorticoids both in vitro and in vivo (63, 64, 65), and corticosteroid hormones, can profoundly alter hippocampal function (66). The ex vivo brain slice preparation (67, 68) is used. The effect of hypoxia over synaptic function and synaptic plasticity is determined by using recording techniques that measure synaptic activity in the hippocampal slice. The CA3 axons traveling into the CA1 area are stimulated, and field excitatory postsynaptic potentials (fEPSPs) measured by placing a recording electrode (glass pipette, 2-3 MΩ tip resistance) in the stratum radiatum of CA1 which is packed with excitatory synapses. fEPSPs mediated by N-methyl-D-aspartate receptors (NMDARs) are studied in pharmacological isolation with the use of agents to block other receptors: CNQX (20 μM) blocks α-amino-3-hydroxyl-5-methyl-4-isoxazole-propionate receptor (AMPAR), LY367385 (100 μM) blocks metabotropic glutamate receptors 1 (mGluR1), MPEP (10 μM) blocks mGluR5, picrotoxin (100 μM) and gabazine (10 μM) block γ-aminobutyric acid receptors type A (GABAaRs), saclofen (200 μM) blocks GABAbRs, methyllycaconitine (10 nM) blocks α7 nicotinic receptors, and strychnine (1 μM) blocks glycine receptors. fEPSPs mediated by AMPARs in pharmacological isolation are studied with the same cocktail of agents, except that instead of CNQX, APV (50 μM) is used to block the NMDAR. Intracellular recording techniques are applied to study the effect of hypoxia on NMDARs, AMPARs and GABARs using the whole-cell recording method, in which the tip of a recording electrode will form a tight seal with the soma of a single, visualized neuron. Responses will be amplified (Dagan BVC-700A, Minneapolis, Minn.), digitized (30 kHz), and stored on PC running Pulse software (Heka, Bellmore, N.Y.). Evoked synaptic events are studied with the "voltage-clamp" technique which permits the neuron to be held at a given holding potential (Vh) while measuring the activation of the synaptic receptor as a current (I). This current is termed excitatory postsynaptic current (EPSC) in the case of NMDARs and AMPARs. It is called inhibitory postsynaptic current (IPSC) in the case of the GABARs. By modifying the Vh values systematically, the associated I values are obtained, thus generating an I-V curve for each receptor in relation to a given hypoxic treatment. Hypoxic events are assessed in altering the I-V curve for each receptor. Standard paradigms for inducing synaptic plasticity are employed. Long-term potentiation (LTP) is triggered by stimulating the CA3 axons with a train of 100 pulses delivered at 100 Hz. This brief period (1 sec) of intense stimulation is usually referred as "tetanus". It is well known that stimulation with a tetanus can enhance the size of the synaptic EPSPs in CA1 and this paradigm is NMDAR-dependent (69). Long-term depression (LTD) is triggered by stimulating the CA3 axons with a train of 600 pulses, delivered at 1 Hz (70). This long pattern is considered "low-frequency stimulation" (LFS) with respect to the tetanus that is used to produce LTP. LFS is able to decrease the size of the synaptic EPSPs in CA1 and is also NMDAR-dependent.

The second set of mice are euthanized and the brain tissue collected and assessed for oxidative changes and altered gene expression. The oxidative changes are assessed by examining Indicators of oxidative stress as described previously (57). Briefly, 1) oxidized proteins are identified protein carbonyl content in cytosolic and mitochondrial compartments are assessed by immunodetection of the 2,4-dinitrophenylhydrazone-derivatized carbonyl groups in proteins (that had been separated with 10% SDS-PAGE and transferred to nitrocellulose membrane; 2) Tissue aconitase activity is measured in mitochondrial and cytosolic fractions using a commercially available kit (Cayman Chemical, Ann Arbor, Mich.); 3) Concentrations of reduced glutathione (GSH) and oxidized glutathione disulfide (GSSG) are determined with the established glutathione reductase-DTNB recycling procedure by using a commercially available kit (Calbiochem, San Diego, Calif.).

EXAMPLES

An animal subject to hypoxia is administered an amount of an inhibitor of MIF. The administration of the inhibitor of MIF is effective to improve the animal's performance on one or more of the behavioral and cognitive function tests described hereinabove.

A subject having a neurological disorder associated with hypoxia is administered an amount of a macrophage migration inhibitory factor (MIF) inhibitor effective to treat the disorder associated with hypoxia. The subject experiences alleviation of the neurological disorder associated with hypoxia.

A subject having a mental disorder associated with hypoxia is administered an amount of a macrophage migration inhibitory factor (MIF) inhibitor effective to treat the disorder associated with hypoxia. The subject experiences alleviation of the mental disorder associated with hypoxia.

A subject having a memory deficit associated with hypoxia is administered an amount of a macrophage migration inhibitory factor (MIF) inhibitor effective to treat the memory deficit associated with hypoxia. The subject experiences alleviation of the memory deficit associated with hypoxia. In an embodiment, the deficit is a deficit in working memory. In an embodiment, the deficit is a deficit in spatial working memory.

REFERENCES

1. Rich, S., Dantzker, D. R., Ayres, S. M., Bergofsky, E. H., Brundage, B. H., Detre, K. M., Fishman, A. P., Goldring, R. M., Groves, B. M., Koerner, S. K., et al. 1987. Primary pulmonary hypertension. A national prospective study. *Ann Intern Med* 107:216-223.
2. Stenmark, K. R., Fagan, K. A., and Frid, M. G. 2006. Hypoxia-induced pulmonary vascular remodeling: cellular and molecular mechanisms. *Circ Res* 99:675-691.
3. Tuder, R. M., Yun, J. H., Bhunia, A., and Fijalkowska, I. 2007. Hypoxia and chronic lung disease. *J Mol Med* 85:1317-1324.
4. Dorfmuller, P., Perros, F., Balabanian, K., and Humbert, M. 2003. Inflammation in pulmonary arterial hypertension. *Eur Respir J* 22:358-363.

5. Lue, H., Kleemann, R., Calandra, T., Roger, T., and Bernhagen, J. 2002. Macrophage migration inhibitory factor (MIF): mechanisms of action and role in disease. *Microbes Infect* 4:449-460.
6. Sakuragi, T., Lin, X., Metz, C. N., Ojamaa, K., Kohn, N., Al-Abed, Y., and Miller, E. J. 2007. Lung-derived macrophage migration inhibitory factor in sepsis induces cardio-circulatory depression PMID: 17381395. *Surg Infect (Larchmt)* 8:29-40.
7. Dewor, M., Steffens, G., Krohn, R., Weber, C., Baron, J., and Bernhagen, J. 2007. Macrophage migration inhibitory factor (MIF) promotes fibroblast migration in scratch-wounded monolayers in vitro. *FEBS Lett* 581:4734-4742.
8. Petrenko, O., Fingerle-Rowson, G., Peng, T., Mitchell, R. A., and Metz, C. N. 2003. Macrophage migration inhibitory factor deficiency is associated with altered cell growth and reduced susceptibility to Ras-mediated transformation. *J Biol Chem* 278:11078-11085.
9. Hudson, J. D., Shoaibi, M. A., Maestro, R., Carnero, A., Hannon, G. J., and Beach, D. H. 1999. A proinflammatory cytokine inhibits p53 tumor suppressor activity. *J Exp Med* 190:1375-1382.
10. Mitchell, R. A., Metz, C. N., Peng, T., and Bucala, R. 1999. Sustained mitogen-activated protein kinase (MAPK) and cytoplasmic phospholipase A2 activation by macrophage migration inhibitory factor (MIF). Regulatory role in cell proliferation and glucocorticoid action. *J Biol Chem* 274:18100-18106.
11. Petrenko, O., and Moll, U. M. 2005. Macrophage migration inhibitory factor MIF interferes with the Rb-E2F pathway. *Mol Cell* 17:225-236.
12. Swant, J. D., Rendon, B. E., Symons, M., and Mitchell, R. A. 2005. Rho GTPase-dependent signaling is required for macrophage migration inhibitory factor-mediated expression of cyclin D1. *J Biol Chem* 280:23066-23072.
13. Amin, M. A., Volpert, O. V., Woods, J. M., Kumar, P., Harlow, L. A., and Koch, A. E. 2003. Migration inhibitory factor mediates angiogenesis via mitogen-activated protein kinase and phosphatidylinositol kinase. *Circ Res* 93:321-329.
14. Pan, J. H., Sukhova, G. K., Yang, J. T., Wang, B., Xie, T., Fu, H., Zhang, Y., Satoskar, A. R., David, J. R., Metz, C. N., et al. 2004. Macrophage migration inhibitory factor deficiency impairs atherosclerosis in low-density lipoprotein receptor-deficient mice. *Circulation* 109:3149-3153.
15. Chen, Z., Sakuma, M., Zago, A. C., Zhang, X., Shi, C., Leng, L., Mizue, Y., Bucala, R., and Simon, D. 2004. Evidence for a role of macrophage migration inhibitory factor in vascular disease. *Arterioscler Thromb Vasc Biol* 24:709-714.
16. Baugh, J. A., Gantier, M., Li, L., Byrne, A., Buckley, A., and Donnelly, S. C. 2006. Dual regulation of macrophage migration inhibitory factor (MIF) expression in hypoxia by CREB and HIF-1. *Biochem Biophys Res Commun* 347:895-903.
17. Ietta, F., Wu, Y., Romagnoli, R., Soleymanlou, N., Orsini, B., Zamudio, S., Paulesu, L., and Caniggia, I. 2007. Oxygen regulation of macrophage migration inhibitory factor in human placenta. *Am J Physiol Endocrinol Metab* 292:E272-280.
18. Winner, M., Koong, A. C., Rendon, B. E., Zundel, W., and Mitchell, R. A. 2007. Amplification of tumor hypoxic responses by macrophage migration inhibitory factor-dependent hypoxia-inducible factor stabilization. *Cancer Res* 67:186-193.
19. Winner, M., Leng, L., Zundel, W., and Mitchell, R. A. 2007. Macrophage migration inhibitory factor manipulation and evaluation in tumoral hypoxic adaptation. *Methods Enzymol* 435:355-369.
20. Welford, S. M., Bedogni, B., Gradin, K., Poellinger, L., Broome Powell, M., and Giaccia, A. J. 2006. HIF1alpha delays premature senescence through the activation of MIF. *Genes Dev* 20:3366-3371.
21. Oda, S., Oda, T., Nishi, K., Takabuchi, S., Wakamatsu, T., Tanaka, T., Adachi, T., Fukuda, K., Semenza, G. L., and Hirota, K. 2008. Macrophage migration inhibitory factor activates hypoxia-inducible factor in a p53-dependent manner. *PLoS One* 3:e2215.
22. Qi, D., Hu, X., Wu, X., Merk, M., Leng, L., Bucala, R., and Young, L. H. 2009. Cardiac macrophage migration inhibitory factor inhibits JNK pathway activation and injury during ischemia/reperfusion. *J Clin Invest* 119:3807-3816.
23. Simons, D., Grieb, G., Hristov, M., Pallua, N., Weber, C., Bernhagen, J., and Steffens, G. Hypoxia-induced endothelial secretion of macrophage migration inhibitory factor and role in endothelial progenitor cell recruitment. *J Cell Mol Med*.
24. Strange, C., and Highland, K. B. 2005. Pulmonary hypertension in interstitial lung disease. *Curr Opin Pulm Med* 11:452-455.
25. Bruchfeld, A., Carrero, J. J., Qureshi, A. R., Lindholm, B., Barany, P., Heimburger, O., Hu, M., Lin, X., Stenvinkel, P., and Miller, E. J. 2009. Elevated serum macrophage migration inhibitory factor (MIF) concentrations in chronic kidney disease (CKD) are associated with markers of oxidative stress and endothelial activation PMC2600496. *Mol Med* 15:70-75.
26. Pak, O., Aldashev, A., Welsh, D., and Peacock, A. 2007. The effects of hypoxia on the cells of the pulmonary vasculature. *Eur Respir J* 30:364-372.
27. Rose, F., Grimminger, F., Appel, J., Heller, M., Pies, V., Weissmann, N., Fink, L., Schmidt, S., Krick, S., Camenisch, G., et al. 2002. Hypoxic pulmonary artery fibroblasts trigger proliferation of vascular smooth muscle cells: role of hypoxia-inducible transcription factors. *Faseb J* 16:1660-1661.
28. Weitzenblum, E., Chaouat, A., Canuet, M., and Kessler, R. 2009 Pulmonary hypertension in chronic obstructive pulmonary disease and interstitial lung diseases. *Semin Respir Crit Care Med* 30:458-470.
29. Cuttica, M. J., Kalhan, R., Shlobin, O. A., Ahmad, S., Gladwin, M., Machado, R. F., Barnett, S. D., and Nathan, S. D. Categorization and impact of pulmonary hypertension in patients with advanced COPD. *Respir Med*.
30. Thabut, G., Dauriat, G., Stern, J. B., Logeart, D., Levy, A., Marrash-Chahla, R., and Mal, H. 2005. Pulmonary hemodynamics in advanced COPD candidates for lung volume reduction surgery or lung transplantation. *Chest* 127:1531-1536.
31. Minai, O. A., Chaouat, A., and Adnot, S. Pulmonary hypertension in COPD: epidemiology, significance, and management: pulmonary vascular disease: the global perspective. *Chest* 137:39S-51S.
32. Scharf, S. M., Iqbal, M., Keller, C., Criner, G., Lee, S., and Fessler, H. E. 2002. Hemodynamic characterization of patients with severe emphysema. *Am J Respir Crit Care Med* 166:314-322.
33. Stenmark, K. R., Gerasimovskaya, E., Nemenoff, R. A., and Das, M. 2002. Hypoxic activation of adventitial fibroblasts: role in vascular remodeling. *Chest* 122:326S-334S.

34. Lue, H., Kapurniotu, A., Fingerle-Rowson, G., Roger, T., Leng, L., Thiele, M., Calandra, T., Bucala, R., and Bernhagen, J. 2006. Rapid and transient activation of the ERK MAPK signalling pathway by macrophage migration inhibitory factor (MIF) and dependence on JAB1/CSN5 and Src kinase activity. *Cell Signal* 18:688-703.
35. Cheng, K. F., and Al-Abed, Y. 2006. Critical modifications of the ISO-1 scaffold improve its potent inhibition of macrophage migration inhibitory factor (MIF) tautomerase activity. *Bioorg Med Chem Lett* 16:3376-3379.
36. Kumar, R. K., O'Grady, R., Li, W., Smith, L. W., and Rhodes, G. C. 1991. Primary culture of adult mouse lung fibroblasts in serum-free medium: responses to growth factors. *Exp Cell Res* 193:398-404.
37. Al-Abed, Y., Dabideen, D., Aljabari, B., Valster, A., Messmer, D., Ochani, M., Tanovic, M., Ochani, K., Bacher, M., Nicoletti, F., et al. 2005. ISO-1 binding to the tautomerase active site of MIF inhibits its pro-inflammatory activity and increases survival in severe sepsis. *J Biol Chem* 280:36541-36544.
38. Li, F. H., Xia, W., Li, A. W., Zhao, C. F., and Sun, R. P. 2007. Inhibition of rho kinase attenuates high flow induced pulmonary hypertension in rats. *Chin Med J (Engl)* 120:22-29.
39. Chang E H, Rigotti A, Huerta P T. (2009) Age-related influence of the HDL receptor SR-BI on synaptic plasticity and cognition. Neurobiol Aging 30:407-19.
40. Contet C, Rawlins J N, Deacon R M. (2001) A comparison of 12952/SvHsd and C57BL/6JO1aHsd mice on a test battery assessing sensorimotor, affective and cognitive behaviours: implications for the study of genetically modified mice. Behav Brain Res 124:33-46.
41. Deacon R M, Rawlins J N. (2002) Learning impairments of hippocampal-lesioned mice in a paddling pool. Behav Neurosci 116:472-78.
42. Irwin S. (1968) Comprehensive observational assessment: Ia. A systematic, quantitative procedure for assessing the behavioral and physiologic state of the mouse. Psychopharmacologia 13:222-57.
43. Lee J Y, Huerta P T, Zhang J, Kowal C, Bertini E, Volpe B T, Diamond B. (2009) Neurotoxic autoantibodies mediate congenital cortical impairment of offspring in maternal lupus. Nat Med 15:91-6.
44. Rogers D C, et al. (1997) Behavioral and functional analysis of mouse phenotype: SHIRPA, a proposed protocol for comprehensive phenotype assessment. Mamm Genome 8:711-3.

What is claimed is:

1. A method for treating a neurological disorder associated with hypoxia, or a mental disorder associated with hypoxia, in a subject comprising administering to the subject an amount of a small molecule macrophage migration inhibitory factor (MIF) inhibitor effective to treat the neurological or mental disorder.

2. The method of claim 1, wherein the disorder associated with hypoxia is mental.

3. The method of claim 1, wherein the disorder associated with hypoxia is neurological.

4. The method of claim 1, wherein the disorder is a cognitive dysfunction.

5. The method of claim 1, wherein the disorder is anxiety.

6. The method of claim 1, wherein the disorder is depression.

7. The method of claim 1, wherein the disorder is memory deficit.

8. The method of claim 1, wherein the MIF inhibitor is administered so as to cross the blood brain barrier of the subject.

9. The method of claim 1, wherein the MIF inhibitor is administered inhalationally.

10. The method of claim 1, wherein the MIF inhibitor is administered orally.

11. The method of claim 1, wherein the MIF inhibitor is administered intravenously.

12. The method of claim 1, wherein the MIF inhibitor has the structure:

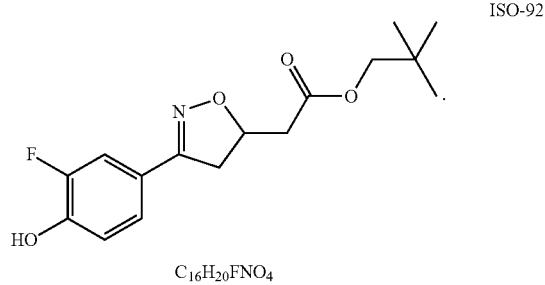 [SMILES: CC(C)(C)COC(=O)CC1CC(c2ccc(O)c(F)c2)=NO1 ; "C16H20FNO4"]

ISO-92

$C_{16}H_{20}FNO_4$

* * * * *

UNITED STATES PATENT AND TRADEMARK OFFICE
CERTIFICATE OF CORRECTION

| | | |
|---|---|---|
| PATENT NO. | : 9,457,013 B2 | Page 1 of 1 |
| APPLICATION NO. | : 14/276104 | |
| DATED | : October 4, 2016 | |
| INVENTOR(S) | : Edmund Miller et al. | |

It is certified that error appears in the above-identified patent and that said Letters Patent is hereby corrected as shown below:

On the Title Page

In (54) the title of invention "METHOD FOR TREATING A NEUROLOGICAL DISORDER ASSOCIATED WITH HYPOXIA USING A SMALL MOLEUCULE MIF INHIBITOR" should read --METHOD FOR TREATING A NEUROLOGICAL DISORDER ASSOCIATED WITH HYPOXIA USING A SMALL MOLECULE MIF INHIBITOR--

In the Specification

Column 1, at Line 16, please add the following paragraph:
--Statement of Government Support
This invention was made with government support under grant number HL111469 awarded by the National Institutes of Health. The government has certain rights in the invention.--

Signed and Sealed this
Ninth Day of October, 2018

Andrei Iancu
*Director of the United States Patent and Trademark Office*

SEQUENCE LISTING

<160> NUMBER OF SEQ ID NOS: 4

<210> SEQ ID NO 1
<211> LENGTH: 115
<212> TYPE: PRT
<213> ORGANISM: Homo Sapiens

<400> SEQUENCE: 1

Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
        35                  40                  45

Ala Phe Gly Gly Ser Ser Glu Pro Cys Ala Leu Cys Ser Leu His Ser
    50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Asn Val Gly Trp Asn Asn Ser
            100                 105                 110

Thr Phe Ala
        115

<210> SEQ ID NO 2
<211> LENGTH: 7845
<212> TYPE: DNA
<213> ORGANISM: Homo Sapiens

<400> SEQUENCE: 2
cacccaccca gccggaattg gctctggcca ctctgggagg gcggggtggg ggttgcaagt      60
cccttgttac gcagggagcc cctcagttag ggagaggaga cagggtctca ggacaggacc     120
ttgaagacaa ggaagggcag tgcagagagg ggtgagagag ccagactggg tttctagggg    180

```
gtggtccagg gtgggagctg acctgcctct gctgagactg cgttccaggt gtgagcattg    240
atgtctagcc catgtagctg gagaggagtc acagccatgc tccccagctc cagcccacct    300
ccccagaccc cagacccagt gtggcctctc cccacctccc agagcatgtg gtcaagcccc    360
tctcctagcc cgaatccctc cctcatttgc taattaccag gacctacatg tcccagcttc    420
ccagggccag gggacagggc cccgcccatc tggcaggctc aagttggctg cctggctgcc    480
gggatccagg cggcgctcac aaggatctgg gcttgcacag cctccaaagg ctgttgtcc     540 attctcttgt atttgttctc atcctctcct ttcttggacc ctctgagtct ctggttccct    600
cttgttggga cccagatcac tctgtgcctc agctgaatca tttttccctt cagtttacac    660
atatccacct agggtccact acatccagag gcttccgcct cagtccttgt cctcaggctg    720
tgcccagggt tgtgaggatg gcggtggtcc ttaccttgca aaacagtctc ccagtgacaa    780
caatgttcag ggataacatc tatggagggc tttctatgta tcaggaccat tctgagtatc    840
ttccaagtgt tagctccttt aatcctggaa aggaccccat gaaattagta cttttattac    900
ccctgttgta catatgagag actgagtaaa agccggtggc ttgtccaggg tcacacagct    960
aactggaatg ccaggagta gacctggtga ccatggaccc cagaccttga tcactgcaca    1020
cgctgcgtct gggacctcgc ctggtacctg aggtccgtgg cgcgctggtg ctgatcattc    1080
agagtgctca tgggaagtgt agtctagagt ctgtgtgctt cctgatctcc ttgatctcca    1140
ttttattgag gaggccttta ggccacccga ggggtccaga gtgaccctgt ggattagcag    1200
tggagctcag cttgagccag cgctcttcag gggtcgtgtt ctgcccccat tctctggttc    1260
attctgcagg tagcagggaa tcattgaaga ttagagagaa tcaaacacct ggagagagat    1320
gactctgccc ggggagccca ggctcctgtc tgggtgcaca ctccagggct agatggtgac    1380
ttctcagcta ctctagcttc ataggctcat agtgcatgtg agcactcatg tggacacacg    1440
tgcacgcgca cacacatgga cacacacaca cacacacaca ccgctgtctt ggaatcaga    1500 ccatgaaaat gcttcctcag aggcctaggg gtgaggaagc tgaggtgagt tgtgcctcca    1560
gctggatgtg ctgggatggg gtgggagatg aggtggccac acctgggtgg caggaactct    1620
ggggcagtga accttctaac gaacagatct gggatgctgc catgaggagg aagagggagt    1680
cagcagccat gcctgccaat gcctcctagc gcatttgtcc atggttagcg ataattatt     1740 gtgtccctat gggtcccaag gtgtattatt ttttttttgc tcttataata aatcaacaca    1800 aattttagc agcttcaaac aacacgcatt tattatctca cagtttctgt gggtcagtag     1860
tccggcgtga catgactagg tcttctgtgt aaggactcgc atggccaaag tcaaggtatc    1920
tgaagggaca agggaaaaat ccacttccaa gttcaatctg gttgtgagca gaattcagtt    1980
ccttgtggtt gtaccatgag gtctctggtc cccttcatct tcaaagccgg taatggacat    2040
cgagtgtttc tcttgcttgg aatctggcac tctagctgga gaaaattatc tgcttttaag    2100
agttcatgtg attagattgg gtgtacccag atgctccatg ctaatctccc tattatgcac    2160
agatgcataa tcctaattgc atctgtgaag tgcttttgc caggtaacat ggcatacttg     2220
taggttccag ggattagtgc ttgtcctccc cctgctattc tttagtgggc aggggtcat     2280 ctgcctacca cggaggtaag gggtcaggag gtatgcatac agcaatgccc aaaaagagac    2340
tgtccccact gggatggagt ttaccgccta gacatgcagt cttaactcag aaatatggag    2400
atagcctcga aggacaggac aggtactggg cacgtgtggg aatggaccaa gccaggtgct    2460
ccggggcctt tccaaggaa ctaaggctga gccaagaact gaaggatgag ttggagtcag     2520
atgagggaaa atgtgggcaa actggatttc agaaccaacc cccaaccctg gagccaggag    2580
```

```
ccatggtact gaaggacagt gcgccataac tcagagaacc agggagggtt ggcggaggct   2640
cacagggacc gggttacccc agggccttgt gacagtacta ccctagtat cagaggagac    2700 tgtcattggc atttaggcca cttggtgctc ataacacctc tatgtcaggt gaacactatt   2760
gtcatcccca aattacagat ggggaaagtg agccaaatgt ccatgctagt aagaggcaaa   2820
tcatatcact tctttgggta cccttctaga aggatgaggc tgactgccac tggaaacagc   2880
tggggagggt acaaggagat gacaagtggc tcagaggctg tcctggctat aagaattaaa   2940
gaggaaagaa acaccaaggg tggctcgaca gtcaacaagg acaggtttat tttggaaaac   3000
aaacttgaga ggggcttctg gccaagttag gtcagagcca cactctctta caaactaagg   3060
atatttaagg gttttggagg gggttcttat cataggttct gaatgtttct gtgtgaggga   3120
aagtttattg cggggatgga atgtctctgg tcagaaggga ggctgtctcc gggttggcat   3180
gtttctggtc agagaagggt ttatcttagg gttggaatgt ttctggttat gctgacatta   3240
gctattaggc tgatattttc gggctggatt taggcggctt ttaattaagg gggaacttag   3300
aatggtggtg tttgttcaag atggcaatgc tcctgctccg tcactggcca ggtaaggcaa   3360 cccttgtta tggtaacaac ctgagattgg caggggctca cctccagggg cagctcatgt    3420
gcttgctggc gaggctgcac cttgtcattc aggttcacag gcacaggtc aaccaggccc    3480 tggctcttca gtcttctgcc tggagtgact tatgtaattc tgctcagctt tcatagggca   3540
cagggagtcg ggctaactc tgctgcctgg ggctggaaac agactcctcc cttgaggagc    3600
agcagtccac catagggaag tcacagtggt ccaggccaaa ggggatgcag gtagtgtaga   3660
ctaggcggta gttcagggaa tggagagaag tgggaataaa gggatagtga aaggaagcat   3720
attttactgg caggtgatga ggtgtaggag acaagtcat acatttggac tttacagagc    3780
agtggacact cagtcagctg ctgtcagcgc ctgggactta ggggagtgcc cctggctgga   3840
gacatggtat ggagtgccat cagttaggga gccctgggca caggtaagag aaggtgtgac   3900
accaggaggg aaagagtctg ggcccagct gcaggaacca atacccatag gctatttgta    3960
taaatgggcc atggggcctc ccagctggag gctggctggt gccacgaggg tcccacaggc   4020
atgggtgtcc ttcctatatc acatggcctt cactgagact ggtatatgga ttgcacctat   4080
cagagaccaa ggacaggacc tccctggaaa tctctgagga cctggcctgt gatccagttg   4140
ctgccttgtc ctcttcctgc tatgtcatgg cttatcttct ttcacccatt cattcattca   4200
ttcattcagc agtattagtc aatgtctctt gtatgcctgg cacctgctag atggtccccg   4260
agtttaccat tagtggaaaa gacatttaag aaattcacca agggctctat gagaggccat   4320
acacggtgga cctgactagg gtgtggcttc cctgaggagc tgaagttgcc cagaggccca   4380
gagaagggga gctgagcacg tttgaaccac tgaacctgct ctggacctcg cctccttccc   4440
ttcggtgcct cccagcatcc tatcctcttt aaagagcagg ggttcaggga agttccctgg   4500
atggtgattc gcaggggcag ctcccctctc acctgccgcg atgactaccc cgccccatct   4560
caaacacaca agctcacgca tgcgggactg gagcccttga ggacatgtgg cccaaagaca   4620
ggaggtacag gggctcagtg cgtgcagtgg aatgaactgg gcttcatctc tggaagggta   4680
aggggccatc ttccgggttc accgccgcat ccccacccc ggcacagcgc ctcctggcga    4740
ctaacatcgg tgacttagtg aaaggactaa gaaagacccg aggcgaggcc ggaacaggcc   4800
gatttctagc cgccaagtgg agaacaggtt ggagcggtgc gccgggctta gcggcggttg   4860
ctggaggaac gggcggagtc gcccagggtc ctgccctgcg ggggtcgagc cgaggcaggc   4920
```

```
ggtgacttcc ccactcgggg cggagccgca gcctcgcggg ggcggggcct ggcgccggcg      4980
gtggcgtcac aaaaggcggg accacagtgg tgtccgagaa gtcaggcacg tagctcagcg      5040
gcggccgcgg cgcgtgcgtc tgtgcctctg cgcgggtctc ctggtccttc tgccatcatg      5100
ccgatgttca tcgtaaacac caacgtgccc cgcgcctccg tgccgacgg gttcctctcc       5160 gagctcaccc agcagctggc gcaggccacc ggcaagcccc ccaggtttg ccgggagggg       5220 acaggaagag gggggtgccc accggacgag gggttccgcg ctgggagctg gggaggcgac      5280
tcctgaacgg agctgggggg cggggcgggg ggaggacggt ggctcgggcc cgaagtggac      5340
gttcggggcc cgacgaggtc gctggggcgg gctgaccgcg ccctttcctc gcagtacatc      5400
gcggtgcacg tggtcccgga ccagctcatg gccttcggcg gctccagcga gccgtgcgcg      5460
ctctgcagcc tgcacagcat cggcaagatc ggcggcgcgc agaaccgctc ctacagcaag      5520
ctgctgtgcg gcctgctggc cgagcgcctg cgcatcagcc cggacaggta cgcggagtcg      5580
cggaggggcg gggagggggc ggcggcgcgc ggccaggccc gggactgagc cacccgctga      5640
gtccggcctc ctccccccgc agggtctaca tcaactatta cgacatgaac gcggccaatg      5700
tgggctggaa caactccacc ttcgcctaag agccgcaggg acccacgctg tctgcgctgg      5760
ctccacccgg gaacccgccg cacgctgtgt tctaggcccg cccacccccaa ccttctggtg     5820 gggagaaata acggtttag agactaggag tgcctcgggg ttccttggct gcgggagga       5880 attggtgcag agccgggata ttggggagcg aggtcgggaa cggtgttggg ggcggggtc      5940 agggccgggt tgctctcctc cgaacctgct gttcgggagc cctttgtcc agcctgtccc      6000 tcctacgctc ctaacagagg agccccagtg tctttccatt ctatggcgta cgaagggatg      6060
aggagaagtt ggcactctgc cctgggctgc agactcggga tctaaggcgc tctgcccgcc      6120
ggaatccgtt gtacctaggg ccaccacgtg gggtgctgga ggtgagccga ccacggaaga     6180
gggggaggag gagttggagt tgggaggagt ccgaggtctt ctaggcctag acctttctct     6240
cagccccacc ttccccagcc ttcttgttgg gcagagggta gccagaggac agaaagatcc      6300
cacccagagc cactcactgc catccacttt gttaggtgac ttcaggagag ttttcaggcg      6360
ggtgggtggg ggaggtgcag agttcttggt cataccgccc cgtccacccc cgaaccccac     6420
gccttgggtt ctgctcccct cagacaccca ccaagcctcc gccacagcag ttccctgagg      6480
aaattgggcg tggggtttcc attgggaccg ttcgtgttct gtggtgccac agacatgtct      6540
gtaaaacctt cagttatgtt tgggcgcagt ggcacaagcc tgtgatcccg gcactttggg      6600
aggtggaggt gagtggagtg tgactcctct gcttctctca gtctccagcc acatctcgtc      6660
tccagtcccc tgttcactcg gtcatcccgc gcagtactgg acagcgagct ctccttccag      6720
aagagcaatg ggctgggtg gggtgaagat taggaagagg aaggagaata gaagctccag       6780
ggagtctgga agggtggcac ccatcttggg atggggcacc ccttccatga aggtctctaa      6840
agcaaggccc tcctcagctt actccctgcc agccgagggc ctcagtctca ttgttaactc      6900
agtgagaggg cggtggagcc cctcgtctac ctcccagctg ggggagacat gggggcatg      6960 ggatggctcc agctgtagcg ggaaggtccc actcctctca gcctggcttt caggcttgag      7020
gtttccttct tggatctgag tacctgtggt gtaacaggca ccctcctcgg ccctggcctt      7080
tatcacatcc cctcagctcc tgggtgcccc cagccccagc ctcccaaggc ctgaggctga      7140
gctttgccca ggaccccag ttccccccac aacaaactct ttctgcctcg ggccccacac      7200
cccaccaagc cctggctggc ccctggctc cacccccgcc tcagcggtct ttgctctcgg      7260
ctgtgtcaca gatagggaga gcaggggcgc agtgccccat gagcatctaa tgcaactccc     7320
```

-continued

```
tcatttcaca gatgaggaca ctgacccag gatccagggc atggtcatac actcaatgcc    7380
atgccccctg caagggccct gtggcctcac atgagcaagt tagactctga gggccgagga    7440
gatgggcagg gcaggctggg cacctgctgt gtgagggcag gagggttggt gagagctgtc    7500
ctccaaaagc aggtgagtgt ctgaggttct gtggccccct gggggcatcc acaaggtcat    7560
gggtccttgg actccaggaa caaaggggt gtctgtgggt cagggaccta tccgcttgcc    7620
ctgcccaaag tgttcctaag tccctgggga ctaataaccg gcctgcctgc tggggaggtc    7680
agctgctaca tcccaccttc aagccacacc tgcccccatt gaccccatc ccatggccag    7740 ctccattttcc tccaaagcac aggctccact gcccaccagg tggtgggtct cttcctcaaa    7800 ccctgtttg actgcccag gacctgcagg gtcagccttg gaaat    7845
```

<210> SEQ ID NO 3
<211> LENGTH: 18
<212> TYPE: DNA
<213> ORGANISM: Artificial Sequence
<220> FEATURE:
<223> OTHER INFORMATION: Primer directed against human MIF

<400> SEQUENCE: 3
accgctccta cagcaagc                                                    18

<210> SEQ ID NO 4
<211> LENGTH: 22
<212> TYPE: DNA
<213> ORGANISM: ARTIFICIAL SEQUENCE
<220> FEATURE:
<223> OTHER INFORMATION: Primer diretced against human MIF

<400> SEQUENCE: 4
cgcgttcatg tcgtaatagt tg                                               22